US008295934B2

(12) United States Patent
Leyde

(10) Patent No.: US 8,295,934 B2
(45) Date of Patent: Oct. 23, 2012

(54) SYSTEMS AND METHODS OF REDUCING ARTIFACT IN NEUROLOGICAL STIMULATION SYSTEMS

(75) Inventor: Kent W. Leyde, Sammamish, WA (US)

(73) Assignee: NeuroVista Corporation, Seattle, WA (US)

( * ) Notice: Subject to any disclaimer, the term of this patent is extended or adjusted under 35 U.S.C. 154(b) by 129 days.

(21) Appl. No.: 11/599,179

(22) Filed: Nov. 14, 2006

(65) Prior Publication Data

US 2008/0114417 A1    May 15, 2008

(51) Int. Cl.
*A61N 1/08* (2006.01)
(52) U.S. Cl. ................... 607/45; 607/2; 607/44
(58) Field of Classification Search .......... 600/544; 607/45, 44, 2, 63
See application file for complete search history.

(56) References Cited

U.S. PATENT DOCUMENTS

| | | |
|---|---|---|
| 3,218,638 A | 11/1965 | Honig |
| 3,498,287 A | 3/1970 | Ertl |
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |

(Continued)

FOREIGN PATENT DOCUMENTS

CA    2251852    4/1999

(Continued)

OTHER PUBLICATIONS

DiLorenzo, Daniel, U.S. Appl. No. 11/743,607, entitled "Controlling a Subject's Susceptibility to a Seizure," filed May 2, 2007.

(Continued)

*Primary Examiner* — Carl H Layno
*Assistant Examiner* — Pamela M Bays
(74) *Attorney, Agent, or Firm* — Shay Glenn LLP

(57) ABSTRACT

The present invention relates to neurological systems and methods of use which acquire physiological signals from a subject and stimulate the subject. The system is adapted to control the timing at which the system acquires the physiological signals from the subject and the timing of the stimulation signal to reduce the amount of stimulation induced artifact that is acquired by the system.

54 Claims, 4 Drawing Sheets

U.S. PATENT DOCUMENTS

| | | | |
|---|---|---|---|
| 4,612,934 A | 9/1986 | Borkan | |
| 4,679,144 A | 7/1987 | Cox et al. | |
| 4,686,999 A | 8/1987 | Snyder et al. | |
| 4,702,254 A | 10/1987 | Zabara | |
| 4,735,208 A | 4/1988 | Wyler et al. | |
| 4,768,176 A | 8/1988 | Kehr et al. | |
| 4,768,177 A | 8/1988 | Kehr et al. | |
| 4,785,827 A | 11/1988 | Fischer | |
| 4,793,353 A | 12/1988 | Borkam | |
| 4,817,628 A | 4/1989 | Zealear | |
| 4,838,272 A | 6/1989 | Lieber | |
| 4,844,075 A | 7/1989 | Liss et al. | |
| 4,852,573 A | 8/1989 | Kennedy | |
| 4,867,164 A | 9/1989 | Zabara | |
| 4,873,981 A | 10/1989 | Abrams et al. | |
| 4,878,498 A | 11/1989 | Abrams et al. | |
| 4,903,702 A | 2/1990 | Putz | |
| 4,920,979 A | 5/1990 | Bullara | |
| 4,926,865 A | 5/1990 | Oman | |
| 4,955,380 A | 9/1990 | Edell | |
| 4,978,680 A | 12/1990 | Sofia | |
| 4,979,511 A | 12/1990 | Terry | |
| 4,991,582 A | 2/1991 | Byers et al. | |
| 5,010,891 A | 4/1991 | Chamoun | |
| 5,016,635 A | 5/1991 | Graupe | |
| 5,025,807 A | 6/1991 | Zabara | |
| 5,031,618 A | 7/1991 | Mullett | |
| 5,070,873 A | 12/1991 | Graupe et al. | |
| 5,082,861 A | 1/1992 | Sofia | |
| 5,097,835 A | 3/1992 | Putz | |
| RE34,015 E | 8/1992 | Duffy | |
| 5,154,172 A | 10/1992 | Terry | |
| 5,167,229 A | 12/1992 | Peckham et al. | |
| 5,179,950 A | 1/1993 | Stanislaw | |
| 5,181,520 A | 1/1993 | Wertheim et al. | |
| 5,186,170 A | 2/1993 | Varichio | |
| 5,188,104 A | 2/1993 | Wernicke | |
| 5,190,029 A | 3/1993 | Byron et al. | |
| 5,193,539 A | 3/1993 | Schulman et al. | |
| 5,193,540 A | 3/1993 | Schulman et al. | |
| 5,205,285 A | 4/1993 | Baker, Jr. | |
| 5,215,086 A | 6/1993 | Terry, Jr. et al. | |
| 5,215,088 A | 6/1993 | Normann | |
| 5,215,089 A | 6/1993 | Baker, Jr. | |
| 5,222,494 A | 6/1993 | Baker, Jr. | |
| 5,222,503 A | 6/1993 | Ives | |
| 5,231,988 A | 8/1993 | Wernicke et al. | |
| 5,235,980 A | 8/1993 | Varichio et al. | |
| 5,237,991 A | 8/1993 | Baker, Jr. | |
| 5,251,634 A | 10/1993 | Weinberg | |
| 5,263,480 A | 11/1993 | Wernicke et al. | |
| 5,265,619 A | 11/1993 | Comby et al. | |
| 5,269,302 A | 12/1993 | Swartz et al. | |
| 5,269,303 A | 12/1993 | Wernicke et al. | |
| 5,269,315 A | 12/1993 | Leuchter et al. | |
| 5,292,772 A | 3/1994 | Sofia | |
| 5,293,879 A | 3/1994 | Vonk | |
| 5,299,118 A | 3/1994 | Martens et al. | |
| 5,299,569 A | 4/1994 | Wernicke et al. | |
| 5,300,094 A | 4/1994 | Kallok et al. | |
| 5,304,206 A | 4/1994 | Baker, Jr. et al. | |
| 5,311,876 A | 5/1994 | Olsen et al. | |
| 5,312,439 A | 5/1994 | Loeb | |
| 5,314,458 A | 5/1994 | Najafi et al. | |
| 5,324,316 A | 6/1994 | Schulman et al. | |
| 5,330,515 A | 7/1994 | Rutecki et al. | |
| 5,335,657 A | 8/1994 | Terry et al. | |
| 5,342,408 A | 8/1994 | deColriolis et al. | |
| 5,342,409 A | 8/1994 | Mullett | |
| 5,343,064 A | 8/1994 | Spangler et al. | |
| 5,349,962 A | 9/1994 | Lockard et al. | |
| 5,351,394 A | 10/1994 | Weinberg | |
| 5,361,760 A | 11/1994 | Normann | |
| 5,365,939 A | 11/1994 | Ochs | |
| 5,376,359 A | 12/1994 | Johnson | |
| 5,392,788 A | 2/1995 | Hudspeth | |
| 5,405,365 A | 4/1995 | Hoegnelid et al. | |
| 5,405,367 A | 4/1995 | Schulman et al. | |
| 5,411,540 A | 5/1995 | Edell et al. | |
| 5,458,117 A | 10/1995 | Chamoun | |
| 5,474,547 A | 12/1995 | Aebischer et al. | |
| 5,476,494 A | 12/1995 | Edell et al. | |
| 5,486,999 A | 1/1996 | Mebane | |
| 5,513,649 A | 5/1996 | Gevins | |
| 5,531,778 A | 7/1996 | Maschino et al. | |
| 5,540,730 A | 7/1996 | Terry | |
| 5,540,734 A | 7/1996 | Zabara | |
| 5,549,656 A | 8/1996 | Reiss | |
| 5,555,191 A | 9/1996 | Hripcsak | |
| 5,571,148 A | 11/1996 | Loeb et al. | |
| 5,571,150 A | 11/1996 | Wernicke | |
| 5,575,813 A | 11/1996 | Edell et al. | |
| 5,578,036 A | 11/1996 | Stone et al. | |
| 5,611,350 A | 3/1997 | John | |
| 5,626,145 A | 5/1997 | Clapp et al. | |
| 5,626,627 A | 5/1997 | Krystal et al. | |
| 5,638,826 A | 6/1997 | Wolpaw | |
| 5,649,068 A | 7/1997 | Boser et al. | |
| 5,672,154 A | 9/1997 | Sillen et al. | |
| 5,683,422 A | 11/1997 | Rise | |
| 5,683,432 A | 11/1997 | Goedeke et al. | |
| 5,690,681 A | 11/1997 | Geddes et al. | |
| 5,690,691 A * | 11/1997 | Chen et al. | 607/40 |
| 5,697,369 A | 12/1997 | Long | |
| 5,700,282 A | 12/1997 | Zabara | |
| 5,704,352 A | 1/1998 | Tremblay et al. | |
| 5,707,400 A | 1/1998 | Terry et al. | |
| 5,711,316 A | 1/1998 | Elsberry et al. | |
| 5,713,923 A | 2/1998 | Ward et al. | |
| 5,715,821 A | 2/1998 | Faupel | |
| 5,716,377 A | 2/1998 | Rise et al. | |
| 5,720,294 A | 2/1998 | Skinner | |
| 5,735,814 A | 4/1998 | Elsberry et al. | |
| 5,743,860 A | 4/1998 | Hively et al. | |
| 5,752,979 A | 5/1998 | Benabid | |
| 5,769,778 A | 6/1998 | Abrams et al. | |
| 5,776,434 A | 7/1998 | Purewal et al. | |
| 5,782,798 A | 7/1998 | Rise | |
| 5,782,874 A | 7/1998 | Loos | |
| 5,782,891 A | 7/1998 | Hassler et al. | |
| 5,792,186 A | 8/1998 | Rise | |
| 5,800,474 A | 9/1998 | Bernabid et al. | |
| 5,813,993 A | 9/1998 | Kaplan | |
| 5,814,014 A | 9/1998 | Elsberry et al. | |
| 5,815,413 A | 9/1998 | Hively et al. | |
| 5,816,247 A | 10/1998 | Maynard | |
| 5,824,021 A | 10/1998 | Rise | |
| 5,832,932 A | 11/1998 | Elsberry et al. | |
| 5,833,709 A | 11/1998 | Rise et al. | |
| 5,857,978 A | 1/1999 | Hively et al. | |
| 5,862,803 A | 1/1999 | Besson et al. | |
| 5,876,424 A | 3/1999 | O'Phelan et al. | |
| 5,899,922 A | 5/1999 | Loos | |
| 5,913,881 A | 6/1999 | Benz et al. | |
| 5,916,239 A | 6/1999 | Geddes et al. | |
| 5,917,429 A | 6/1999 | Otis, Jr. et al. | |
| 5,928,272 A | 7/1999 | Adkins | |
| 5,931,791 A | 8/1999 | Saltzstein et al. | |
| 5,938,689 A | 8/1999 | Fischell et al. | |
| 5,941,906 A | 8/1999 | Barreras et al. | |
| 5,950,632 A | 9/1999 | Reber et al. | |
| 5,957,861 A | 9/1999 | Combs et al. | |
| 5,971,594 A | 10/1999 | Sahai et al. | |
| 5,975,085 A | 11/1999 | Rise | |
| 5,978,702 A | 11/1999 | Ward et al. | |
| 5,978,710 A | 11/1999 | Prutchi et al. | |
| 5,995,868 A | 11/1999 | Dorfmeister et al. | |
| 6,006,124 A | 12/1999 | Fischell et al. | |
| 6,016,449 A | 1/2000 | Fischell et al. | |
| 6,018,682 A | 1/2000 | Rise | |
| 6,042,548 A | 3/2000 | Giuffre | |
| 6,042,579 A | 3/2000 | Elsberry et al. | |
| 6,051,017 A | 4/2000 | Loeb et al. | |
| 6,052,619 A | 4/2000 | John | |
| 6,061,593 A | 5/2000 | Fischell et al. | |
| 6,066,163 A | 5/2000 | John | |
| 6,081,744 A | 6/2000 | Loos | |

| | | | | | | |
|---|---|---|---|---|---|---|
| 6,094,598 | A | 7/2000 | Elsberry et al. | 6,665,562 B2 | 12/2003 | Gluckman et al. |
| 6,109,269 | A | 8/2000 | Rise et al. | 6,668,191 B1 | 12/2003 | Boveja |
| 6,117,066 | A | 9/2000 | Abrams et al. | 6,671,555 B2 | 12/2003 | Gielen |
| 6,128,537 | A | 10/2000 | Rise et al. | 6,678,548 B1 | 1/2004 | Echauz et al. |
| 6,128,538 | A | 10/2000 | Fischell et al. | 6,684,105 B2 | 1/2004 | Cohen et al. |
| 6,134,474 | A | 10/2000 | Fischell et al. | 6,687,538 B1 | 2/2004 | Hrdlicka et al. |
| 6,161,045 | A | 12/2000 | Fischell et al. | 6,735,467 B2 | 5/2004 | Wilson |
| 6,167,304 | A | 12/2000 | Loos | 6,760,626 B1 | 7/2004 | Boveja |
| 6,171,239 | B1 | 1/2001 | Humphrey | 6,768,969 B1 | 7/2004 | Nikitin et al. |
| 6,176,242 | B1 | 1/2001 | Rise | 6,778,854 B2 | 8/2004 | Puskas |
| 6,205,359 | B1 | 3/2001 | Boveja | 6,782,292 B2 | 8/2004 | Whitehurst |
| 6,208,893 | B1 | 3/2001 | Hofmann | 6,879,859 B1 | 4/2005 | Boveja |
| 6,221,011 | B1 | 4/2001 | Bardy | 6,893,395 B1 | 5/2005 | Kraus et al. |
| 6,227,203 | B1 | 5/2001 | Rise et al. | 6,901,294 B1 | 5/2005 | Whitehurst et al. |
| 6,230,049 | B1 | 5/2001 | Fischell et al. | 6,901,296 B1 | 5/2005 | Whitehurst et al. |
| 6,248,126 | B1 | 6/2001 | Lesser et al. | 6,912,419 B2 | 6/2005 | Hill |
| 6,249,703 | B1 | 6/2001 | Stanton | 6,921,538 B2 | 7/2005 | Donovan |
| 6,263,237 | B1 | 7/2001 | Rise | 6,921,541 B2 | 7/2005 | Chasin et al. |
| 6,280,198 | B1 | 8/2001 | Calhoun et al. | 6,923,784 B2 | 8/2005 | Stein |
| 6,304,775 | B1 | 10/2001 | Iasemidis et al. | 6,931,274 B2 | 8/2005 | Williams |
| 6,309,406 | B1 | 10/2001 | Jones et al. | 6,934,580 B1 | 8/2005 | Osorio |
| 6,328,699 | B1 | 12/2001 | Eigler | 6,937,891 B2 | 8/2005 | Leinders et al. |
| 6,337,997 | B1 | 1/2002 | Rise | 6,944,501 B1 | 9/2005 | Pless |
| 6,339,725 | B1 | 1/2002 | Naritoku | 6,950,706 B2 | 9/2005 | Rodriguez |
| 6,341,236 | B1 | 1/2002 | Osorio et al. | 6,973,342 B1 | 12/2005 | Swanson |
| 6,343,226 | B1 | 1/2002 | Sunde et al. | 6,990,372 B2 | 1/2006 | Perron et al. |
| 6,353,754 | B1 | 3/2002 | Fischell et al. | 7,010,351 B2 | 3/2006 | Firlik et al. |
| 6,354,299 | B1 | 3/2002 | Fischell et al. | 7,089,059 B1 | 8/2006 | Pless |
| 6,356,784 | B1 | 3/2002 | Lozano et al. | 7,117,108 B2 | 10/2006 | Rapp et al. |
| 6,356,788 | B2 | 3/2002 | Boveja | 7,174,212 B1 | 2/2007 | Klehn et al. |
| 6,358,203 | B2 | 3/2002 | Bardy | 7,177,701 B1 | 2/2007 | Pianca |
| 6,358,281 | B1 | 3/2002 | Berrang et al. | 7,209,787 B2 * | 4/2007 | DiLorenzo ................. 607/45 |
| 6,360,122 | B1 | 3/2002 | Fischell | 7,212,851 B2 | 5/2007 | Donoghue et al. |
| 6,366,813 | B1 | 4/2002 | DiLorenzo | 7,231,254 B2 | 6/2007 | DiLorenzo |
| 6,366,814 | B1 | 4/2002 | Boveja | 7,324,851 B1 | 1/2008 | DiLorenzo |
| 6,374,140 | B1 | 4/2002 | Rise | 7,373,198 B2 | 5/2008 | Bibian et al. |
| 6,386,882 | B1 | 5/2002 | Linberg | 7,463,917 B2 | 12/2008 | Martinez |
| 6,402,678 | B1 | 6/2002 | Fischell et al. | 7,631,015 B2 | 12/2009 | Gupta et al. |
| 6,411,854 | B1 | 6/2002 | Tziviskos et al. | 7,805,196 B2 | 9/2010 | Miesel et al. |
| 6,427,086 | B1 | 7/2002 | Fischell et al. | 7,881,798 B2 | 2/2011 | Miesel et al. |
| 6,434,419 | B1 | 8/2002 | Gevins et al. | 8,055,348 B2 | 11/2011 | Heruth et al. |
| 6,442,421 | B1 | 8/2002 | Quyen et al. | 2001/0051819 A1 | 12/2001 | Fischell et al. |
| 6,443,891 | B1 | 9/2002 | Grevious | 2001/0056290 A1 | 12/2001 | Fischell et al. |
| 6,453,198 | B1 | 9/2002 | Torgerson | 2002/0002390 A1 | 1/2002 | Fischell et al. |
| 6,463,328 | B1 * | 10/2002 | John ............................... 607/45 | 2002/0035338 A1 | 3/2002 | Dear et al. |
| 6,466,822 | B1 * | 10/2002 | Pless ............................... 607/45 | 2002/0054694 A1 | 5/2002 | Vachtsevanos et al. |
| 6,471,645 | B1 | 10/2002 | Warkentin et al. | 2002/0072770 A1 | 6/2002 | Pless |
| 6,473,639 | B1 | 10/2002 | Fischell et al. | 2002/0072776 A1 | 6/2002 | Osorio et al. |
| 6,473,644 | B1 | 10/2002 | Terry et al. | 2002/0072782 A1 | 6/2002 | Osorio et al. |
| 6,480,743 | B1 | 11/2002 | Kirkpatrick | 2002/0077670 A1 | 6/2002 | Archer et al. |
| 6,484,132 | B1 | 11/2002 | Hively et al. | 2002/0095099 A1 | 7/2002 | Quyen et al. |
| 6,488,617 | B1 | 12/2002 | Katz | 2002/0099412 A1 | 7/2002 | Fischell et al. |
| 6,496,724 | B1 | 12/2002 | Levendowski et al. | 2002/0103512 A1 | 8/2002 | Echauz et al. |
| 6,505,077 | B1 | 1/2003 | Kast et al. | 2002/0109621 A1 | 8/2002 | Khair et al. |
| 6,510,340 | B1 | 1/2003 | Jordan | 2002/0111542 A1 | 8/2002 | Warkentin et al. |
| 6,511,424 | B1 | 1/2003 | Moore-Ede | 2002/0116042 A1 | 8/2002 | Boling |
| 6,529,774 | B1 | 3/2003 | Greene | 2002/0126036 A1 | 9/2002 | Flaherty et al. |
| 6,534,693 | B2 | 3/2003 | Fischell et al. | 2002/0147388 A1 | 10/2002 | Mass et al. |
| 6,547,746 | B1 | 4/2003 | Marino | 2002/0169485 A1 | 11/2002 | Pless et al. |
| 6,549,804 | B1 | 4/2003 | Osorio et al. | 2002/0177882 A1 | 11/2002 | DiLorenzo |
| 6,553,262 | B1 | 4/2003 | Lang et al. | 2002/0188330 A1 | 12/2002 | Gielen et al. |
| 6,560,486 | B1 | 5/2003 | Osorio et al. | 2003/0004428 A1 | 1/2003 | Pless |
| 6,571,123 | B2 | 5/2003 | Ives et al. | 2003/0009207 A1 | 1/2003 | Paspa et al. |
| 6,571,125 | B2 | 5/2003 | Thompson | 2003/0013981 A1 | 1/2003 | Gevins et al. |
| 6,572,528 | B2 | 6/2003 | Rohan et al. | 2003/0018367 A1 | 1/2003 | DiLorenzo |
| 6,587,719 | B1 | 7/2003 | Barrett et al. | 2003/0028072 A1 | 2/2003 | Fischell et al. |
| 6,591,132 | B2 | 7/2003 | Gotman et al. | 2003/0050549 A1 | 3/2003 | Sochor |
| 6,591,137 | B1 | 7/2003 | Fischell et al. | 2003/0050730 A1 | 3/2003 | Greeven et al. |
| 6,591,138 | B1 | 7/2003 | Fischell et al. | 2003/0073917 A1 | 4/2003 | Echauz et al. |
| 6,597,954 | B1 | 7/2003 | Fischell et al. | 2003/0074033 A1 | 4/2003 | Pless et al. |
| 6,600,956 | B2 | 7/2003 | Maschino | 2003/0083716 A1 | 5/2003 | Nicolelis et al. |
| 6,609,025 | B2 | 8/2003 | Barrett et al. | 2003/0114886 A1 | 6/2003 | Gluckman et al. |
| 6,618,623 | B1 | 9/2003 | Pless et al. | 2003/0144709 A1 | 7/2003 | Zabara et al. |
| 6,620,415 | B2 | 9/2003 | Donovan | 2003/0144711 A1 | 7/2003 | Pless et al. |
| 6,622,036 | B1 | 9/2003 | Suffin | 2003/0144829 A1 | 7/2003 | Geatz et al. |
| 6,622,038 | B2 | 9/2003 | Barrett et al. | 2003/0149457 A1 | 8/2003 | Tcheng et al. |
| 6,622,041 | B2 | 9/2003 | Terry et al. | 2003/0158587 A1 | 8/2003 | Esteller et al. |
| 6,622,047 | B2 | 9/2003 | Barrett et al. | 2003/0167078 A1 | 9/2003 | Weisner et al. |
| 6,658,287 | B1 | 12/2003 | Litt et al. | 2003/0174554 A1 | 9/2003 | Dunstone et al. |

| | | |
|---|---|---|
| 2003/0176806 A1 | 9/2003 | Pineda et al. |
| 2003/0181955 A1 | 9/2003 | Gielen |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1 | 4/2004 | Echauz et al. |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1* | 7/2004 | Deadwyler et al. ............ 600/544 |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021108 A1 | 1/2005 | Klosterman et al. |
| 2005/0021313 A1 | 1/2005 | Nikitin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0119703 A1 | 6/2005 | DiLorenzo |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad |
| 2005/0197590 A1 | 9/2005 | Osorio et al. |
| 2005/0203366 A1 | 9/2005 | Donoghue et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222626 A1 | 10/2005 | DiLorenzo |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |
| 2006/0122469 A1 | 6/2006 | Martel |
| 2006/0129056 A1 | 6/2006 | Leuthardt et al. |
| 2006/0142822 A1* | 6/2006 | Tulgar .............................. 607/61 |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |
| 2006/0224191 A1 | 10/2006 | Dilorenzo |
| 2006/0253096 A1 | 11/2006 | Blakley et al. |
| 2006/0293578 A1 | 12/2006 | Rennaker, II |
| 2006/0293720 A1 | 12/2006 | DiLorenzo et al. |
| 2007/0027367 A1 | 2/2007 | Oliver et al. |
| 2007/0027514 A1 | 2/2007 | Gerber |
| 2007/0035910 A1 | 2/2007 | Stevenson |
| 2007/0043459 A1 | 2/2007 | Abbott, III et al. |
| 2007/0055320 A1 | 3/2007 | Weinand |
| 2007/0060973 A1 | 3/2007 | Ludvig et al. |
| 2007/0073355 A1 | 3/2007 | DiLorenzo |
| 2007/0073357 A1 | 3/2007 | Rooney et al. |
| 2007/0100398 A1 | 5/2007 | Sloan |
| 2007/0142862 A1 | 6/2007 | DiLorenzo |
| 2007/0149952 A1 | 6/2007 | Bland et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0185890 A1 | 8/2007 | VanEpps et al. |
| 2007/0213629 A1 | 9/2007 | Greene |
| 2007/0213785 A1 | 9/2007 | Osorio et al. |
| 2007/0217121 A1 | 9/2007 | Fu et al. |
| 2007/0238939 A1 | 10/2007 | Giftakis et al. |
| 2007/0244407 A1 | 10/2007 | Osorio |
| 2007/0250077 A1 | 10/2007 | Skakoon et al. |
| 2007/0250901 A1 | 10/2007 | McIntire et al. |
| 2007/0287931 A1 | 12/2007 | DiLorenzo |
| 2008/0021341 A1 | 1/2008 | Harris et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0082019 A1 | 4/2008 | Ludving et al. |
| 2008/0091090 A1 | 4/2008 | Guillory et al. |
| 2008/0103556 A1 | 5/2008 | Li et al. |
| 2008/0161712 A1 | 7/2008 | Leyde |
| 2008/0161713 A1 | 7/2008 | Leyde et al. |
| 2008/0221876 A1 | 9/2008 | Holdrich |
| 2008/0319281 A1 | 12/2008 | Aarts |
| 2009/0264952 A1 | 10/2009 | Jassemidis et al. |
| 2010/0023089 A1 | 1/2010 | DiLorenzo |
| 2010/0125219 A1 | 5/2010 | Harris et al. |
| 2010/0145176 A1 | 6/2010 | Himes |
| 2011/0166430 A1 | 7/2011 | Harris et al. |
| 2011/0260855 A1 | 10/2011 | John et al. |
| 2011/0319785 A1 | 12/2011 | Snyder et al. |

FOREIGN PATENT DOCUMENTS

| | | |
|---|---|---|
| CA | 2423840 | 2/2002 |
| CA | 2428116 | 5/2002 |
| CA | 2428383 | 5/2002 |

| | | |
|---|---|---|
| CA | 2425122 | 6/2002 |
| CA | 2425004 | 8/2002 |
| CA | 2456443 | 1/2003 |
| CA | 2491987 | 1/2004 |
| DE | 69832022D | 12/2005 |
| EP | 0124663 A1 | 11/1984 |
| EP | 0898460 | 3/1999 |
| EP | 1017313 | 7/2000 |
| EP | 1107693 | 6/2001 |
| EP | 1145735 A2 | 10/2001 |
| EP | 1145736 A2 | 10/2001 |
| EP | 1292900 | 3/2003 |
| EP | 1307260 | 5/2003 |
| EP | 1331967 | 8/2003 |
| EP | 1335668 | 8/2003 |
| EP | 1341580 | 9/2003 |
| EP | 1404216 | 4/2004 |
| EP | 1333753 | 9/2004 |
| EP | 1525551 | 4/2005 |
| EP | 1558121 | 8/2005 |
| EP | 1558128 | 8/2005 |
| EP | 1558130 | 8/2005 |
| EP | 1558131 | 8/2005 |
| EP | 1558132 | 8/2005 |
| EP | 1558330 | 8/2005 |
| EP | 1558334 | 8/2005 |
| EP | 1562674 | 8/2005 |
| EP | 0911061 B1 | 10/2005 |
| EP | 1609414 A2 | 12/2005 |
| JP | 24033673 A2 | 2/2004 |
| SU | 1074484 | 2/1984 |
| WO | WO 85/01213 A1 | 3/1985 |
| WO | WO 92/00119 A1 | 1/1992 |
| WO | WO 97/26823 A1 | 7/1997 |
| WO | WO 97/34522 A1 | 9/1997 |
| WO | WO 97/34524 A1 | 9/1997 |
| WO | WO 97/34525 A1 | 9/1997 |
| WO | WO 97/39797 A1 | 10/1997 |
| WO | WO 97/42990 A1 | 11/1997 |
| WO | WO 97/45160 A1 | 12/1997 |
| WO | WO 98/49935 A1 | 11/1998 |
| WO | WO 99/20342 A1 | 4/1999 |
| WO | WO 99/56821 A1 | 11/1999 |
| WO | WO 99/56822 A1 | 11/1999 |
| WO | WO 00/07494 A2 | 2/2000 |
| WO | WO 00/10455 | 3/2000 |
| WO | WO 01/41867 A1 | 6/2001 |
| WO | WO 01/48676 A1 | 7/2001 |
| WO | WO 01/49364 A2 | 7/2001 |
| WO | WO 01/67288 A2 | 9/2001 |
| WO | WO 01/75660 A1 | 10/2001 |
| WO | WO 02/09610 A1 | 2/2002 |
| WO | WO 02/09811 A1 | 2/2002 |
| WO | WO 02/36003 A1 | 5/2002 |
| WO | WO 02/38031 A2 | 5/2002 |
| WO | WO 02/38217 A2 | 5/2002 |
| WO | WO 02/49500 A2 | 6/2002 |
| WO | WO 02/058536 A2 | 8/2002 |
| WO | WO 02/067122 A1 | 8/2002 |
| WO | WO 03/001996 A2 | 1/2003 |
| WO | WO 03/009207 A1 | 1/2003 |
| WO | WO 03/030734 A2 | 4/2003 |
| WO | WO 03/035165 A1 | 5/2003 |
| WO | WO 03/084605 A1 | 10/2003 |
| WO | WO 2004/008373 A2 | 1/2004 |
| WO | WO 2004/032720 A2 | 4/2004 |
| WO | WO 2004/034231 A2 | 4/2004 |
| WO | WO 2004/034879 A2 | 4/2004 |
| WO | WO 2004/034880 A2 | 4/2004 |
| WO | WO 2004/034881 A2 | 4/2004 |
| WO | WO 2004/034882 A2 | 4/2004 |
| WO | WO 2004/034883 A2 | 4/2004 |
| WO | WO 2004/034885 A2 | 4/2004 |
| WO | WO 2004/034982 A2 | 4/2004 |
| WO | WO 2004/034997 A2 | 4/2004 |
| WO | WO 2004/034998 A2 | 4/2004 |
| WO | WO 2004/035130 A2 | 4/2004 |
| WO | WO 2004/036370 A2 | 4/2004 |
| WO | WO 2004/036372 A2 | 4/2004 |
| WO | WO 2004/036376 A2 | 4/2004 |
| WO | WO 2004/036377 A2 | 4/2004 |
| WO | WO 2004/037342 A2 | 5/2004 |
| WO | WO 2004/043536 A1 | 5/2004 |
| WO | WO 2004/091718 A1 | 10/2004 |
| WO | WO 2005/007236 A2 | 1/2005 |
| WO | WO 2005/028026 A1 | 3/2005 |
| WO | WO 2005/028028 A1 | 3/2005 |
| WO | WO 2005/031630 A2 | 4/2005 |
| WO | WO 2005/051167 A1 | 6/2005 |
| WO | WO 2005/051306 A2 | 6/2005 |
| WO | WO 2005/117693 A1 | 12/2005 |
| WO | WO 2006/014971 A2 | 2/2006 |
| WO | WO 2006/014972 A2 | 2/2006 |
| WO | WO 2006/020794 A2 | 2/2006 |
| WO | WO 2006/035392 A1 | 4/2006 |
| WO | WO 2007/150003 A2 | 12/2007 |

OTHER PUBLICATIONS

DiLorenzo, Daniel, U.S. Appl. No. 11/743,611, entitled "Providing Output Indicative of Subject's Disease State," filed May 2, 2007.

DiLorenzo, Daniel, U.S. Appl. No. 11/282,317 entitled "Closed-loop vag nerve stimulation," filed Nov. 17, 2005.

Harris, John, U.S. Appl. No. 11/734,190, entitled "Methods and Template Assembly for Implanting an Electrode Array in a Patient," filed Apr. 11, 2007.

Leyde et al.; U.S. Appl. No. 12/020,507 entitled "Methods and systems for measuring a subject's susceptibility to a seizure," filed Jan. 25, 2008.

Snyder et al.; U.S. Appl. No. 12/020,450 entitled "Systems and methods for identifying a contra-ictal condition in a subject," filed Jan. 25, 2008.

Snyder et al.; U.S. Appl. No. 12/035,335 entitled "Methods and systems for characterizing and generating a patient-specific seizure prediction system," filed Feb. 21, 2008.

Adjouadi, et al. A new mathematical approach based on orthogonal operators for the detection of interictal spikes in epileptogenic data. Biomed. Sci. Instrum. 2004; 40: 175-80.

Adjouadi, et al. Detection of interictal spikes and artifactual data through orthogonal transformations. J. Clin. Neurophysiol. 2005; 22(1):53-64.

Adjouadi, et al. Interictal spike detection using the Walsh transform. IEEE Trans. Biomed. Eng. 2004; 51(5): 868-72.

Aksenova, et al. Nonparametric on-line detection of changes in signal spectral characteristics for early prediction of epilepsy seizure onset. J. Automation and Information Sciences. 2004; 36(8): 35-45.

Aksenova, et al. On-line disharmony detection for early prediction of epilepsy seizure onset. 5th International Workshop Neural Coding 2003. Aulla (Italy) Sep. 20-25, 2003. (Abstract).

Andrzejak, et al. Bivariate surrogate techniques: necessity, strengths, and caveats. Physical Review E. 2003; 68: 066202-1-066202-15.

Andrzejak, et al. Testing the null hypothesis of the nonexistence of a preseizure state. Physical Review E. 2003; 67: 010901-1-010901-4.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. J Mol. Biol. 13: 238-252.

Baruchi, et al. Functional holography of complex networks activity—From cultures to the human brain. Complexity. 2005; 10(3): 38 R 51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modeling, Identification, and Control. 2003; 377-201: 313-317.

Bhattacharya, et al. Enhanced phase synchrony in the electroencephalograph gamma band for musicians while listening to music. Phys. Rev. E. 2001; 64:012902-1-4.

Boley, et al. Training Support Vector Machine using Adaptive Clustering. 2004 Siam International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporal lobe epilepsy. Electroencephalogr. Clin. Neurophysiol. 1997; 102(2): 98-105.

Cerf, et al. Criticality and synchrony of fluctuations in rhythmical brain activity: pretransitional effects in epileptic patients. Biol. Cybern. 2004; 90(4): 239-55.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al. Spatio-temporal dynamics prior to neocortical seizures: amplitude versphase couplings. IEEE Trans. Biomed. Eng. 2003; 50(5):571-83.

Crichton, Michael, "Terminal Man", 1972, Ballantine Books, NY, NY, pp. 21-24, 32-33, 70-71, and 74-81.

D'Alessandro, et al. Epileptic seizure prediction using hybrid feature selection over multiple intracranial EEG electrode contacts: a report of four patients. IEEE Trans. Biomed. Eng. 2003; 50(5): 603-15.

D'Alessandro, et al. A multi-feature and multi-channel univariate selection process for seizure prediction. Clin. Neurophysiol. 2005; 116(3): 506-16.

Drury, et al. Seizure prediction using scalp electroencephalogram. Exp. Neurol. 2003; 184 Suppl 1: S9-18.

Ebersole, J. S. Functional neuroimaging with EEG source models to localize epileptogenic foci noninvasively. Neurology. Available at http://www.uchospitals.edu/pdf/uch_001471.pdf. Accessed Feb. 28, 2006.

Ebersole, J. S. In search of seizure prediction: a critique. Clin. Neurophysiol. 2005; 116(3): 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Esteller, et al. Feature Parameter Optimization for Seizure Detection/prediction. Proceedings of the 23rd Annual International Conference of the IEEE Engineering in Medicine and Biology Society, Istanbul, Turkey. Oct. 2001.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagnerve stimulation for epilepsy, A report of the therapeutics and technology assessment subcommittee of the American Academy of Neurology. Neurology,53: 666-669.

Gardner, A. B. A Novelty Detection Approach to Seizure Analysis from Intracranial EEG. Georgia Institute of Technology. Apr. 2004. A dissertation available at http://etd.gatech.edu/theses /available/etd-04122004-132404 /unrestricted/gardner_andrew_b_200405phd.pdf, Accessed Feb. 28, 2006.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116(3):527-31.

Harrison, et al. Correlation dimension and integral do not predict epileptic seizures. Chaos. 2005; 15(3): 33106-1-15.

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hively, et al. Epileptic Seizure Forewarning by Nonlinear Techniques. ORNL/TM-2000/333 Oak Ridge National Laboratory. Nov. 2000. Available at http://computing.ornl.gov/cse_home/staff/hively/NBICradaAnnualRpt FY00.pdf. Accessed Feb. 28, 2006.

Hjorth, B. Source derivation simplifies topographical EEG interpretation. Am. J. EEG Technol. 1980; 20: 121-132.

Hsu, et al. A practical guide to support vector classification. Technical report, Department of Computer Science and Information Technology, National Taiwan University, 2003. Available at http://www.csie.ntu.edu.tw/~cjlin/papers/guide/guide.pdf. Accessed Feb. 28, 2006.

Huynh, J. A. Evaluation of Gene Selection Using Support Vector Machine Recursive Feature Elimination. Arizona State University. May 26, 2004. (28 pages).

Huynh, J. A. Evaluation of Gene Selection Using Support Vector Machine Recursive Feature Elimination. Presentation slides. (41 pages) (May 26, 2004).

Iasemidis, et al. Adaptive epileptic seizure prediction system. IEEE Trans. Biomed. Eng. 2003; 50(5):616-27.

Iasemidis, et al. Automated Seizure Prediction Paradigm. Epilepsia. 1998; vol. 39, pp. 56.

Iasemidis, et al. Chaos Theory and Epilepsy. The Neuroscientist. 1996; 2:118-126.

Iasemidis, et al. Comment on "Inability of Lyapunov exponents to predict epileptic seizures." Physical Review Letters. 2005; 94(1):019801-1.

Iasemidis, et al. Detection of the Preictal Transition State in Scalp-Sphenoidal EEG Recordings. American Clinical Neurophysiology Society Annual Meeting, Sep. 1996. pp. C206.

Iasemidis, et al. Dynamical Interaction of the Epileptogenic Focwith Extrafocal Sites in Temporal Lobe Epilepsy (TLE). Ann. Neurol. 1997; 42, pp. 429. pp. M146.

Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.

Iasemidis, et al. Localizing Preictal Temporal Lobe Spike Foci Using Phase Space Analysis. Electroencephalography and Clinical Neurophysiology. 1990; 75, pp. S63-S64.

Iasemidis, et al. Long-term prospective on-line real-time seizure prediction. Clin. Neurophysiol. 2005; 116 (3):532-44.

Iasemidis, et al. Long-Time-Scale Temporo-spatial Patterns of Entrainment of Preictal Electrocorticographic Data in Human Temporal Lobe Epilepsy. Epilepsia. 1990; 31(5):621.

Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.

Iasemidis, et al. Modelling of ECoG in temporal lobe epilepsy. Biomed. Sci. Instrum. 1988; 24: 187-93.

Iasemidis, et al. Nonlinear Dynamics of EcoG Data in Temporal Lobe Epilepsy. Electroencephalography and Clinical Neurophysiology. 1998; 5, pp. 339.

Iasemidis, et al. Phase space topography and the Lyapunov exponent of electrocorticograms in partial seizures. Brain Topogr. 1990; 2(3): 187-201.

Iasemidis, et al. Preictal Entrainment of a Critical Cortical Mass is a Necessary Condition for Seizure Occurrence. Epilepsia. 1996; 37, suppl. 5. pp. 90.

Iasemidis, et al. Preictal-Postictal Vers Postictal Analysis for Epileptogenic Foc Localization. J. Clin. Neurophysiol. 1997; 14, pp. 144.

Iasemidis, et al. Quadratic binary programming and dynamic system approach to determine the predictability of epileptic seizures. Journal of Combinatorial Optimization. 2001; 5: 9-26.

Iasemidis, et al. Quantification of Hidden Time Dependencies in the EEG within the Framework of Non-Linear Dynamics. World Scientific. 1993; pp. 30-47.

Iasemidis, et al. Spatiotemporal dynamics of human epileptic seizures. World Scientific. 1996; pp. 26-30.

Iasemidis, et al. Spatiotemporal Evolution of Dynamical Measures Precedes Onset of Mesial Temporal Lobe Seizures. Epilepsia. 1994; 358, pp. 133.

Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artificial Systems. Ohmsha IOS Press. 1997; 37, pp. 81-88.).

Iasemidis, et al. The evolution with time of the spatial distribution of the largest Lyapunov exponent on the human epileptic cortex. World Scientific. 1991; pp. 49-82.

Iasemidis, et al. The Use of Dynamical Analysis of EEG Frequency Content in Seizure Prediction. American Electroencephalographic Society Annual Meeting, Oct. 1993.

Iasemidis, et al. Time Dependencies in Partial Epilepsy. 1993; 34, pp. 130-131.

Iasemidis, et al. Time dependencies in the occurrences of epileptic seizures. Epilepsy Res. 1994; 17(1): 81-94.

Iasemidis, L. D. Epileptic seizure prediction and control. IEEE Trans. Biomed. Eng. 2003; 50(5):549-58.

Jerger, et al. Early seizure detection. Journal of Clin. Neurophysiol. 2001; 18(3):259-68.

Jerger, et al. Multivariate linear discrimination of seizures. Clin. Neurophysiol. 2005; 116(3):545-51.

Jouny, et al. Characterization of epileptic seizure dynamics using Gabor atom density. Clin. Neurophysiol. 2003; 114(3):426-37.

Jouny, et al. Signal complexity and synchrony of epileptic seizures: Is there an identifiable preictal period? Clin. Neurophysiol. 2005; 116(3):552-8.

Kapiris, et al. Similarities in precursory features in seismic shocks and epileptic seizures. Europhys. Lett. 2005; 69(4):657-663.

Katz, et al. Does interictal spiking change prior to seizures? Electroencephalogr. Clin. Neurophysiol. 1991; 79 (2):153-6.

Kerem, et al. Forecasting epilepsy from the heart rate signal. Med. Biol. Eng. Comput, 2005; 43(2):230-9.

Khalilov, et al. Epileptogenic actions of GABA and fast oscillations in the developing hippocampus. Neuron. 2005; 48(5):787-96.

Korn, et al. Is there chaos in the brain? II. Experimental evidence and related models. C. R. Biol. 2003; 326 (9):787-840.

Kraskov, A. Synchronization and Interdependence Measures and Their Application to the Electroencephalogram of Epilepsy Patients and Clustering of Data. Available at http://www.kfa-juelich.de/nic-series/volume24/nic-series-band24.pdf. Accessed Apr. 17, 2006 (106 pp).

Kreuz, et al. Measure profile surrogates: a method to validate the performance of epileptic seizure prediction algorithms. Phys. Rev. E. 2004; 69(6 Pt 1):061915-1-9.

Lachaux, et al. Measuring phase synchrony in brain signals. Hum. Brain Mapp. 1999; 8(4):194-208.

Lai, et al. Controlled test for predictive power of Lyapunov exponents: their inability to predict epileptic seizures. Chaos. 2004; 14(3):630-42.

Lai, et al. Inability of Lyapunov exponents to predict epileptic seizures. Phys. Rev. Lett. 2003; 91(6):068102-1-4.

Latka, et al. Wavelet analysis of epileptic spikes. Phys. Rev. E. 2003; 67(5 Pt 1):052902 (6 pages).

Le Van Quyen, et al. Anticipating epileptic seizures in real time by a non-linear analysis of similarity between EEG recordings. Neuroreport. 1999; 10(10):2149-55.

Le Van Quyen, et al. Author's second reply. The Lancet. 2003; 361:971.

Le Van Quyen, et al. Comparison of Hilbert transform and wavelet methods for the analysis of neuronal synchrony. J. Neurosci. Methods. 2001; 111(2):83-98.

Le Van Quyen, et al. Nonlinear analyses of interictal EEG map the brain interdependences in human focal epilepsy. Physica D. 1999; 127:250-266.

Le Van Quyen, et al. Preictal state identification by synchronization changes in long-term intracranial EEG recordings. Clin. Neurophysiol. 2005; 116(3):559-68.

Le Van Quyen, M. Anticipating epileptic seizures: from mathematics to clinical applications. C. R. Biol. 2005; 328(2):187-98.

Lehnertz, et al. Nonlinear EEG analysis in epilepsy: its possible use for interictal foc localization, seizure anticipation, and prevention. J. Clin. Neurophysiol. 2001; 18(3):209-22.

Lehnertz, et al. Seizure prediction by nonlinear EEG analysis. IEEE Eng. Med. Biol. Mag. 2003; 22(1):57-63.

Lehnertz, et al. The First International Collaborative Workshop on Seizure Prediction: summary and data description. Clin. Neurophysiol. 2005; 116(3):493-505.

Lehnertz, K. Non-linear time series analysis of intracranial EEG recordings in patients with epilepsy—an overview. Int. J. Psychophysiol. 1999; 34(1):45-52.

Lemos, et al. The weighted average reference montage. Electroencephalogr. Clin. Neurophysiol. 1991; 79 (5):361-70.

Li, et al. Fractal spectral analysis of pre-epileptic seizures in terms of criticality. J. Neural Eng. 2005; 2(2):11-16.

Li, et al. Linear and nonlinear measures and seizure anticipation in temporal lobe epilepsy. J. Comput. Neurosci. 2003; 15(3):335-45.

Li, et al. Non-linear, non-invasive method for seizure anticipation in focal epilepsy. Math. Biosci. 2003; 186 (1):63-77.

Litt, et al. Prediction of epileptic seizures. Lancet Neurol. 2002; 1(1):22-30.

Litt, et al. Seizure prediction and the preseizure period. Curr. Opin. Neurol. 2002; 15(2)173-7.

Maiwald, et al. Comparison of three nonlinear seizure prediction methods by means of the seizure prediction characteristic. Physica D. 2004; 194:357-368.

Mangasarian, et al. Lagrangian Support Vector Machines. Journal of Machine Learning Research. 2001; 1:161-177.

Martinerie, et al. Epileptic seizures can be anticipated by non-linear analysis. Nat. Med. 1998; 4(10):1173-6.

McSharry, et al. Comparison of predictability of epileptic seizures by a linear and a nonlinear method. IEEE Trans. Biomed. Eng. 2003; 50(5):628-33.

McSharry, et al. Linear and non-linear methods for automatic seizure detection in scalp electro-encephalogram recordings. Med. Biol. Eng. Comput. 2002; 40(4):447-61.

McSharry, P. E. Detection of dynamical transitions in biomedical signals using nonlinear methods. Lecture Notes in Computer Science 2004; 3215:483-490.

Meng, et al. Gaussian mixture models of ECoG signal features for improved detection of epileptic seizures. Med. Eng. Phys. 2004; 26(5):379-93.

Mizuno-Matsumoto, et al. Wavelet-crosscorrelation analysis can help predict whether bursts of pulse stimulation will terminate after discharges. Clin. Neurophysiol. 2002; 113(1):33-42.

Mormann, et al. Automated detection of a preseizure state based on a decrease in synchronization in intracranial electroencephalogram recordings from epilepsy patients. Phys. Rev. E. 2003; 67(2 Pt 1):021912-1-10.

Mormann, et al. Epileptic seizures are preceded by a decrease in synchronization. Epilepsy Res. 2003; 53 (3):173-85.

Mormann, et al. Mean phase coherence as a measure for phase synchronization and its application to the EEG of epilepsy patients. Physica D. 2000; 144:358-369.

Mormann, et al. On the predictability of epileptic seizures. Clin. Neurophysiol. 2005; 116(3):569-87.

Mormann, et al. Seizure anticipation: from algorithms to clinical practice. Curr. Opin. Neurol. 2006; 19(2):187-93.

Navarro, et al. Seizure anticipation in human neocortical partial epilepsy. Brain. 2002; 125:640-55.

Navarro, et al. Seizure anticipation: do mathematical measures correlate with video-EEG evaluation? Epilepsia. 2005; 46(3):385-96.

Niederhauser, et al. Detection of seizure precursors from depth-EEG using a sign periodogram transform. IEEE Trans. Biomed. Eng. 2003; 50(4):449-58.

Nigam, et al. A neural-network-based detection of epilepsy. Neurological Research. 2004; 26(1):55-60.

Osorio, et al. Automated seizure abatement in humans using electrical stimulation. Ann. Neurol. 2005; 57 (2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modelling of spike propagation from interictal MEG data. Phys. Med. Biol. 2005; 50(14):3447-69.

Pflieger, et al. A noninvasive method for analysis of epileptogenic brain connectivity. Presented at the American Epilepsy Society 2004 Annual Meeting, New Orleans. Dec. 6, 2004. Epilepsia. 2004; 45(Suppl. 7):70-71.

Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen adn K. R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18 (3):223-45.

Rahimi, et al. On the Effectiveness of Aluminum Foil Helmets: An Empirical Study. Available at http://people.csail.mit.edu/rahimi/helmet/. Accessed Mar. 2, 2006.

Robinson, et al. Steady States and Global Dynamics of Electrical Activity in the Cerebral Cortex. Phys. Rev. E. 1998; (58):3557-3571.

Rudrauf, et al. Frequency flows and the time-frequency dynamics of multivariate phase synchronization in brain signals. NeuroImage. 2005. (19 pages.).

Saab, et al. A system to detect the onset of epileptic seizures in scalp EEG. Clin. Neurophysiol, 2005; 116:427-442.

Sackellares et al. Computer-Assisted Seizure Detection Based on Quantitative Dynamical Measures. American Electroencephalographic Society Annual Meeting, Sep. 1994.

Sackellares et al. Dynamical Studies of Human Hippocampin Limbic Epilepsy. Neurology. 1995; 45, Suppl. 4, pp. A 404.

Sackellares et al. Epileptic Seizures as Neural Resetting Mechanisms. Epilepsia. 1997; vol. 38, Sup. 3.

Sackellares et al. Measurement of Chaos to Localize Seizure Onset. Epilepsia. 1989; 30(5):663.

Sackellares et al. Relationship Between Hippocampal Atrophy and Dynamical Measures of EEG in Depth Electrode Recordings. American Electroencephalographic Society Annual Meeting, Sep. 1995. pp. A105.

Sackellares, J. C. Epilepsy—when chaos fails. In: chaos in the brain? Eds. K. Lehnertz & C.E. Elger. World Scientific. 2000 (22 pages).

Salant, et al. Prediction of epileptic seizures from two-channel EEG. Med. Biol. Eng. Comput. 1998; 36 (5):549-56.

Schelter, et al. Testing for directed influences among neural signals using partial directed coherence. J. Neurosci. Methods. 2006; 152(1-2):210-9.

Schindler, et al. EEG analysis with simulated neuronal cell models helps to detect pre-seizure changes. Clin. Neurophysiol. 2002; 113(4):604-14.

Schwartzkroin, P. Origins of the Epileptic State. Epilepsia. 1997; 38, supply. 8, pp. 853-858.

Sheridan, T. Humans and Automation. NY: John Wiley. 2002.

Shoeb et al. Patient-specific seizure detection. MIT Computer Science and Artificial Intelligence Laboratory. 2004; pp. 193-194.

Staba, et al. Quantitative analysis of high-frequency oscillations (80-500 Hz) recorded in human epileptic hippocampand entorhinal cortex. J. Neurophysiol. 2002; 88(4):1743-52.

Stefanski, et al. Using chaos synchronization to estimate the largest Lyapunov exponent of nonsmooth systems. Discrete Dynamics in Nature and Society. 2000; 4:207-215.

Subasi, et al. Classification of EEG signals using neural network and logistic regression. Computer Methods Programs Biomed. 2005; 78(2):87-99.

Szoka et al. Procedure for preparation of liposomes with large internal aqueospace and high capture volume by reverse phase evaporation. 1978. Proc. Natl Acad. Sci. USA. 75: 4194-4198.

Tass, et al. Detection of n: m Phase Locking from Noisy Data: Application to Magnetoencephalography. Physical Review Letters. 1998; 81(15):3291-3294.

Terry, et al. An improved algorithm for the detection of dynamical interdependence in bivariate time-series. Biol. Cybern. 2003; 88(2):129-36.

Tetzlaff, et al. Cellular neural networks (CNN) with linear weight functions for a prediction of epileptic seizures. Intl. J. of Neural Systems. 2003; 13(6):489-498.

Theiler, et al. Testing for non-linearity in time series: the method of surrogate data. Physica D. 1992; 58:77-94.

Tsakalis, K. S. Prediction and control of epileptic seizures: Coupled oscillator models. Arizona State University. (Slide: 53 pages) (No date).

Van Drongelen, et al. Seizure anticipation in pediatric epilepsy: use of Kolmogorov entropy. Pediatr. Neurol. 2003; 29(3): 207-13.

Van Putten, M. Nearest neighbor phase synchronization as a measure to detect seizure activity from scalp EEG recordings. J. Clin. Neurophysiol. 2003; 20(5):320-5.

Venugopal, et al. A new approach towards predictability of epileptic seizures: KLT dimension. Biomed Sci. Instrum. 2003; 39:123-8.

Vonck, et al. Long-term amygdalohippocampal stimulation for refractory temporal lobe epilepsy. Ann. Neurol. 2002; 52(5):556-65.

Vonck, et al. Long-term deep brain stimulation for refractory temporal lobe epilepsy. Epilepsia. 2005; 46(Suppl 5):98-9.

Vonck, et al. Neurostimulation for refractory epilepsy. Acta. Neurol. Belg. 2003; 103(4):213-7.

Weiss, P. Seizure prelude found by chaos calculation. Science News. 1998; 153(20):326.

Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.

Widman, et al. Reduced signal complexity of intracellular recordings: a precursor for epileptiform activity? Brain Res. 1999; 836(1-2):156-63.

Winterhalder, et al. Sensitivity and specificity of coherence and phase synchronization analysis. (In Press) Phys. Lett. A. 2006.

Winterhalder, et al. The seizure prediction characteristic: a general framework to assess and compare seizure prediction methods. Epilepsy Behav. 2003; 4(3):318-25.

Yang, et al. A supervised feature subset selection technique for multivariate time series. Available at http://infolab.usc.edu/DocsDemos/fsdm05.pdf. Accessed Mar. 2, 2006.

Yang, et al. CLe Ver: A feature subset selection technique for multivariate time series. T. B. Ho, D. Cheung, and H. Liu (Eds.): PAKDD. 2005; LNAI 3518: 516-522.

Yang, et al. Relation between Responsiveness to Neurotransmitters and Complexity of Epileptiform Activity in Rat Hippocampal CA1 Neurons. Epilepsia. 2002; 43(11):1330-1336.

Yatsenko, et al. Geometric Models, Fiber Bundles, and Biomedical Applications. Proceedings of Institute of Mathematics of NAS of Ukraine. 2004; 50 (Part 3):1518R1525.

Zaveri et al. Time-Frequency Analyses of Nonstationary Brain Signals. Electroencephalography and Clinical Neurophysiology. 1991; 79, pp. 28P-29P.

Zhang, et al. High-resolution EEG: cortical potential imaging of interictal spikes. Clin. Neurophysiol. 2003; 114 (10):1963-73.

Snyder et al.; U.S. Appl. No. 12/053,312 entitled "Implantable systems and methods for identifying a contra-ictal condition in a subject," filed Mar. 21, 2008.

DiLorenzo, Daniel; U.S. Appl. No. 12/177,060 entitled "Closed-loop feedback-driven neuromodulation," filed Jul. 21, 2008.

Bland et al.; U.S. Appl. No. 12/180,996 entitled "Patient advisory device," filed Jul. 28, 2008.

Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.

Franaszczuk et al.; An autoregressive method for the measurement of synchronization of interictal and ictal EEG signals; Biological Cybernetics, vol. 81; No. 1; pp. 3-9; 1999.

Mormann et al.; Seizure prediction: the long and winding road; Brain; vol. 130; No. 2; pp. 314-333; Sep. 28, 2006.

Schelter et al.; Testing statistical significance of multivariate time series analysis techniques for epileptic seizure prediction; Chaos: An Interdisciplinary Journal of Nonlinear Science; vol. 16; No. 013108; pp. 1-10; Jan. 2006.

Wong et al.; A stochastic framework for evaluating seizure prediction algorithms using hiden markov models; Journal of Neurophysiology; vol. 97, No. 3; pp. 2525-2532; Oct. 4, 2006.

Yang et al.; Testing whether a prediction scheme is better than guess; Ch. 14 in Quantitative Neuroscience: Models, Algorithms, Diagnostics, and Therapeutic Applications; pp. 252-262; 2004.

Leyde et al.; U.S. Appl. No. 12/343,376 entitled "Systems and method for recording clinical manifestations of a seizure," filed Dec. 23, 2008.

Brown et al.; U.S. Appl. No. 12/343,386 entitled "Housing for an implantable medical device," filed Dec. 23, 2008.

Himes et al.; U.S. Appl. No. 12/646,783 entitled "Brain State Analysis Based on Select Seizure Onset Characteristics and Clinical Manifestations," filed Dec. 23, 2009.

Echauz et al.; U.S. Appl. No. 12/649,098 entitled "Processing for Multi-Channel Signals," filed Dec. 29, 2009.

Floyd et al.; U.S. Appl. No. 12/685,543 entitled "Medical Lead Termination Sleeve for Implantable Medical Devices," filed Jan. 11, 2010.

Himes et al.; U.S. Appl. No. 12/716,132 entitled "Displaying and Manipulating Brain Function Data Including Enhanced Data Scrolling Functionality," filed Mar. 2, 2010.

Himes et al.; U.S. Appl. No. 12/716,147 entitled "Displaying and Manipulating Brain Function Data Including Filtering of Annotations," filed Mar. 2, 2010.

DiLorenzo, Daniel; U.S. Appl. No. 12/774,550 entitled "Systems for Monitoring a Patient's Neurological Disease State," filed May 5, 2010.

Echauz et al.; U.S. Appl. No. 12/792,582 entitled "Processing for Multi-Channel Signals," filed Jun. 2, 2010.

Rothman et al.; Local Cooling: a therapy for intractable neocortical epilepsy; Epilepsy Currents; vol. 3; No. 5; pp. 153-156; Sep./Oct. 2003.

Snyder et al; The statistics of a practical seizure warning system; Journal of Neural Engineering; vol. 5; pp. 392-401; 2008.

Higgins et al.; U.S. Appl. No. 13/026,961 entitled "Neurological monitoring and alerts," filed Feb. 14, 2011.

Leyde et al.; U.S. Appl. No. 13/070,333 entitled "Communication Error Alerting in an Epilepsy Monitoring System," filed Mar. 23, 2011.

Leyde et al.; U.S. Appl. No. 13/070,357 entitled "Patient Entry Recording in an Epilepsy Monitoring System," filed Mar. 23, 2011.

Spector et al.; High and Low Perceived Self-Control of Epileptic Seizures; Epilepsia, vol. 42(4), Apr. 2001; pp. 556-564.

Chen et al.; Clinical utility of video-EEG monitoring; Perdiatric Neurology; vol. 12; No. 3; pp. 220-224; 1995.

* cited by examiner $D = d/T$

SYSTEMS AND METHODS OF REDUCING ARTIFACT IN NEUROLOGICAL STIMULATION SYSTEMS

CROSS-REFERENCE

This application is related to commonly owned U.S. Pat. No. 6,366,813, filed Jun. 25, 1999 and U.S. Pat. No. 6,819,956, filed Nov. 11, 2001.

This application is also related to commonly owned U.S. patent application Ser. Nos. 11/321,897 and 11/322,150, both filed Dec. 28, 2005

BACKGROUND OF THE INVENTION

The present invention relates generally to reducing artifacts in a sampled physiological signal from a subject. More specifically, the present invention relates to methods and systems for delivering stimulation in separate epochs of time from data acquisition epochs of time.

Closed loop neurological stimulation systems that acquire physiological signals from a subject and stimulate a subject can produce stimulation-induced artifact signals when the acquisition of the physiological signal from the subject and stimulation of the subject occur substantially at the same time.

For example, electroencephalographic (EEG) signals acquired from subjects are small in amplitude and relatively low in frequency. Scalp EEG signals, for example, have amplitudes on the order of about 10 uV to about 100 uV and have frequency content in the range of about 0.1 to about 70 Hz. Electrocorticography (ECoG) is the practice of recording signals directly from the surface of the cerebral cortex. ECoG signals are larger, in the range of about 10 uV to about 1000 uV, and depending on the size and geometry of the measuring electrode, which may vary from a disk contact several mm in diameter to a needle-like micro-electrode with dimensions on the orders of microns, these signals may contain useful information at frequencies from 0.01 Hz up to up to several hundred Hz. In practice, the term EEG or intracranial EEG is often used in place of the term ECoG; for simplicity we will use the term "EEG" throughout the remainder of this document to encompass both intracranial EEG and scalp EEG.

Electrical stimulation signals used to stimulate nerve cells are typically similar in frequency to EEG signals but can be much larger in amplitude. Typical stimulation frequencies, or pulse repetition frequencies, range from about 1 Hz to about 1000 Hz. Stimulation pulse widths are typically on the order of about 50 us to about 500 us. Pulse shapes are typically rectangular rather than smoothed or sinusoidal, and therefore generate significant amount of energy at harmonics of the pulse repetition frequency. Typical stimulation waveform amplitudes may be in the range of about 1 V to about 10 V, and when coupled to stimulating electrodes with typical electrode impedances of about 500 Ohms to about 2000 Ohms, this leads to stimulation current amplitudes of between about 0.5 mA and about 20 mA. In order to avoid damage to neural tissue or to the stimulating electrodes, the charge per stimulation pulse should be limited to below about 100 uC to about 200 uC per square cm of electrode area.

A stimulation signal may cause artifact when sensed at substantially the same time as a physiological signal because the electrical stimulation signal can be substantially larger and in substantially the same frequency band as the physiological signal (e.g., an EEG signal).

Stimulation-induced artifact can be reduced by filtering out the artifact signal. Some existing technologies may also synchronize the timing of the filtering process with the timing of the stimulation signal in order to reduce stimulation-induced artifact. These systems, however, do not control the time at which the signal acquisition and stimulation occur, but rather rely on filtering out the artifact signal after it has already been acquired. In addition, some systems simply disable the detection device while stimulation occurs.

There remains a need for a neurological stimulation system which acquires physiological signals from a subject and stimulates the subject to reduce the amount of stimulation-induced artifact sensed by the system.

SUMMARY OF THE INVENTION

One aspect of the invention is a system to reduce artifact in a signal acquired from a subject. The system includes a sensing assembly adapted to acquire a signal from a subject indicative of the subject's brain activity, a stimulation assembly adapted to stimulate one or more neurons of the subject, and a timing controller programmed to control the time at which the sensing assembly acquires the signal to be substantially different than when the stimulation assembly stimulates the subject.

In some embodiments of the system the timing controller is programmed to control the time at which the sensing assembly acquires the signal to be multiple discrete acquisition times and to control the time at which the stimulation assembly stimulates the one or more neurons to be multiple discrete stimulation times. The timing controller can be programmed to control the sensing assembly to acquire the signal in between the stimulation assembly stimulating the one or more neurons. In some embodiments the multiple discrete acquisition times and multiple discrete stimulation times each occur in a regular pattern. In some embodiments the acquisition times and the stimulation times provide epochs of time between the acquisition times and stimulation times in which no acquisition or stimulation occurs.

In some embodiments the multiple discrete acquisition times are about 0.25 seconds to about 5 minutes. In some embodiments the multiple discrete acquisition times are about 5 seconds.

In some embodiments the multiple discrete stimulation times are about 0.5 seconds to about 5 minutes. In some embodiments the multiple discrete acquisition times are about 20 seconds.

In some embodiments the sensing assembly and the stimulation assembly each comprise an electrode array. The same electrode array can be used to stimulate the one or more neurons and acquire the signal from the subject. In some embodiments the stimulation assembly comprises an electrode array adapted to be coupled to a peripheral nerve. In some embodiments the peripheral nerve is a vagus nerve.

In some embodiments the signal is an EEG signal from the subject.

In some embodiments the system further comprises a control assembly adapted to adjust the multiple discrete acquisition times and the multiple discrete stimulation times. The control assembly can be in communication with a device external to the subject wherein the device is adapted to allow adjustment of the stimulation and acquisition times. In some embodiments the control assembly is adapted to dynamically adjust the stimulation or acquisition times.

In some embodiments of the system the subject's brain activity is analyzed to predict an onset of a seizure.

In some embodiments the system also includes a signal processor in communication with the sensing assembly adapted to process the signal to estimate an epileptic neural state. The signal processor can comprise an observer algorithm operative when the sensing assembly is acquiring the signal. In some embodiments the observer algorithm comprises one or more feature extractors and a classifier.

Another aspect of the invention is a method of reducing artifact in a signal acquired from a subject. The method comprises acquiring a signal from a subject indicative of the subject's brain activity, stimulating the subject, and controlling the time at which the acquiring the signal occurs to be substantially different than the stimulating the subject.

In some embodiments the acquiring comprises acquiring the signal at multiple discrete acquisition times and the stimulating comprises stimulating the one or more neurons at multiple discrete stimulation times. The acquiring the signals can occur between the stimulating the subject. In some embodiments the acquiring and stimulating each occur in a regular pattern.

In some embodiments the multiple discrete acquisition times are about 0.25 seconds to about 5 minutes. In some embodiments the multiple discrete acquisition times are about 5 seconds.

In some embodiments the multiple discrete stimulation times are about 0.5 seconds to about 5 minutes. In some embodiments the multiple discrete stimulation times are about 20 seconds.

In some embodiments the acquiring comprises acquiring an EEG signal from the subject. In some embodiments the stimulating comprises stimulating a peripheral nerve such as a vagus nerve.

In some embodiments the method further comprises adjusting the multiple discrete acquisition times and/or the multiple discrete stimulation times.

In some embodiments the subject's brain activity is processed to measure the subject's susceptibility to a seizure.

In some embodiments the method further comprises processing the signal to estimate an epileptic neural state.

Another aspect of the invention is a method of managing seizures. The method comprises acquiring an EEG signal from a subject during multiple discrete acquisition times occurring in a regular pattern, stimulating one or more neurons of the subject during multiple discrete stimulation times occurring in a regular pattern, and controlling the times at which the acquiring the EEG signal occurs to be substantially different than the stimulating the one or more neurons of the subject.

Incorporation By Reference

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
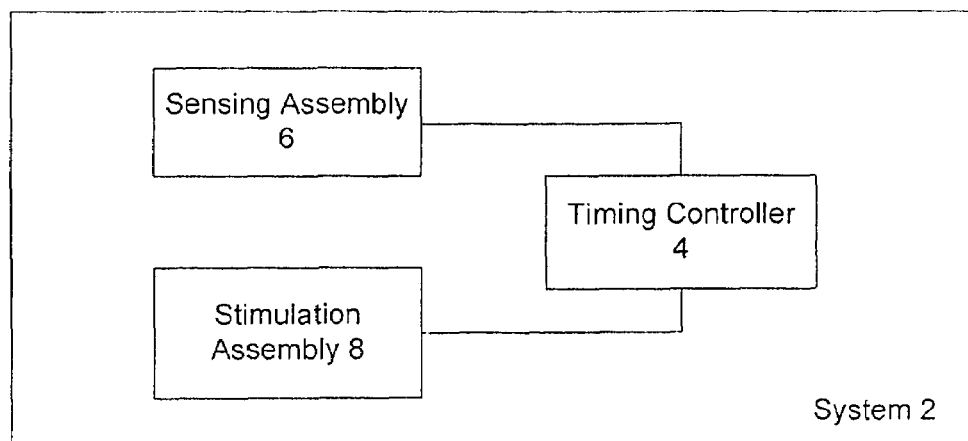
FIG. 1 illustrates a sensing assembly, timing controller, and stimulation assembly.

The systems of the present invention generally reduce artifact in a signal, e.g., an electrical signal, acquired from a subject. In particular, the system can reduce stimulation-induced artifact sensed with a neurological stimulation system that is at least partially implanted in a subject. One aspect of the invention is a system that comprises a sensing assembly adapted to acquire a signal from a subject that contains data that is indicative of the subject's brain activity state or neural state, a stimulation assembly adapted to stimulate one or more neurons of a nervous system component of the subject, and a timing controller programmed to control the time of acquiring the signal(s) from the subject and delivering electrical stimulation to the subject.

The present invention can reduce artifact in the acquired signal by controlling the time at which the signal is acquired from the subject to be substantially different than the time at which the subject is stimulated. Controlling the timing of the signal acquisition and stimulation can reduce the amount of stimulation signal that is sensed by the sensing assembly, thus reducing artifact signals. Furthermore, as data acquisition and stimulating requires the use of power, which may be limited in an implantable neurological stimulation system, controlling the sensing assembly and stimulation assembly to acquire a signal and stimulate at specific times, rather than sensing and stimulating continuously, allows for a more efficient use of the system's power supply.

The methods of the present invention are applicable to closed-loop control systems for controlling a subject's state, closed-loop detection and prediction systems that are used to detect and/or predict the onset of neurological events, and other closed-loop systems which acquire data and deliver a neuromodulation signal to the subject. Each of such systems will typically include one or more algorithms for analyzing signals from the subject and/or determining the subject's response to the analyzed signals. Such algorithms will be referred to herein collectively as an "observer algorithm."

While the remaining discussion focuses on closed-loop control of seizures and detecting and/or predicting an onset of seizures, the present invention may be equally applicable to monitoring and treatment of other neurological and non-neurological conditions. For example, some other conditions that may be treated using the systems of the present invention include, but is not limited to, Alzheimer' disease, Parkinson's disease, migraine headaches, sleep apnea, Huntington's disease, hemiballism, choreoathetosis, dystonia, akinesia, bradykinesia, restless legs syndrome, other movement disorder, dementia, depression, mania, bipolar disorder, other affective disorder, motility disorders, anxiety disorder, phobia disorder, borderline personality disorder, schizophrenia, multiple personality disorder, and other psychiatric disorder, Parkinsonism, rigidity, or hyperkinesias, substance abuse, attention deficit hyperactivity disorder, impaired control of aggression, impaired control of sexual behavior, or the like.

FIG. 1 shows an exemplary system 2 including a timing controller 4 in communication with a sensing assembly 6 and a stimulation assembly 8. The sensing assembly is generally adapted to acquire a signal from a subject which is indicative of the subject's brain activity or the subject's neural state. The term "neural state" is used herein to generally refer to calculation results or indices that are reflective of the state of the subject's neural system, but does not necessarily constitute a complete or comprehensive accounting of the subject's total neurological condition. The estimation and characterization of "neural state" may be based on one or more subject dependent parameters from the brain, such as electrical signals from the brain. In preferred embodiments the sensing assembly is coupled to at least one electrode array to acquire the electrical signal from the subject.

While the electrode arrays may be implanted anywhere within the subject's body, preferred electrode arrays include intracranial or extracranial EEG electrode arrays. The EEG electrode arrays can be adapted to be placed on the subject's head, implanted under the skin, screwed into the skull, or implanted intracranially. For example, in minimally invasive embodiments the electrode array can be implanted beneath at least one layer of the scalp, above the subject's cranium/calvarium, and over one or more target area of the subject's brain. The electrode array may be implanted between any of the layers of the scalp. For example, the electrode array may be positioned between the skin and the connective tissue, between the connective tissue and the epicranial aponeurosis/galea aponeurotica, between the epicranial aponeurosis/galea aponeurotica and the loose aerolar tissue, between the loose aerolar tissue and the pericranium, and/or between the pericranium and the calvarium. In some configurations, it may be useful to implant different electrode arrays between different layers of the scalp.

In more invasive embodiments the electrode array of the sensing assembly includes an intracranial (IC) recording electrode array (e.g., epidural, subdural, depth electrodes, etc.) or a bone screw array which samples intracranial neural signals, including but not limited to cortical, white matter, and deep brain signals. Neural activity to be sensed includes but is not limited to that found in the primary motor cortex, premotor cortex, supplementary motor cortex, somatosensory cortex, white matter tracts associated with these cortical areas, the globus pallidus internal segment, the globus pallidus external segment, the caudate, the putamen, and other cortical and subcortical areas.

The EEG electrode arrays used with the system 2 may include any number of electrodes, and can be placed at a variety of locations in or on the subject such that an EEG signal can be acquired from the subject. The EEG electrode array typically includes between about 8 electrodes and 64 electrodes, but may have more or less, as desired. Some useful electrode arrays include a 1×8 electrode strip, a 2×4 electrode grid, a 3×3 grid array, a 1×8 depth electrode array, an array of bone screws, sphenoidal electrode array, and a nerve cuff electrode array, but many other configurations and types of electrodes may also be useful with the system.

While EEG electrode arrays are one currently preferred embodiment, other types of electrode arrays may also be used in addition to or as an alternative to the EEG electrode arrays. For example, the electrode arrays may include any of the following types of electrodes, either alone or in combination with each other, an electromyography (EMG) array for acquiring EMG signals, an accelerometer array for acquiring acceleration signals, an acoustic transducer array, a peripheral nerve electrode array (e.g., vagus nerve), a cranial nerve electrode array (e.g., trigeminal nerve) or other biological sensors or electrodes for monitoring blood pressure, pulse oximetry, temperature of the brain or other portion of the subject, blood flow measurements in the brain or other parts of the body, ECG/EKG, heart rate signals and/or change in heart rate signals, respiratory rate signals and/or change in respiratory rate signals, chemical concentrations of neuro transmitters, chemical concentrations of medications, pH in the blood or other portions of the body, other vital signs, other physiological or biochemical parameters of the subject's body, or the like.

For example, as noted above, another type of sensing electrode array that may be used with the system is a peripheral nerve electrode array which may be used to acquire peripheral neural signals, including but not limited to efferent and afferent axonal signals from a vagus nerve. The single or plurality of individual peripheral nerve electrode arrays which comprise peripheral nerve electrode array may be implanted in any number of locations throughout the subject. Such peripheral nerve electrode arrays may also be used to deliver a stimulation output signal to the subject. Additional electrode arrays which can also be included in the sensing assembly can be found in commonly owned U.S. Pat. No. 6,366,813, which issued Apr. 2, 2002.

Figure 2:
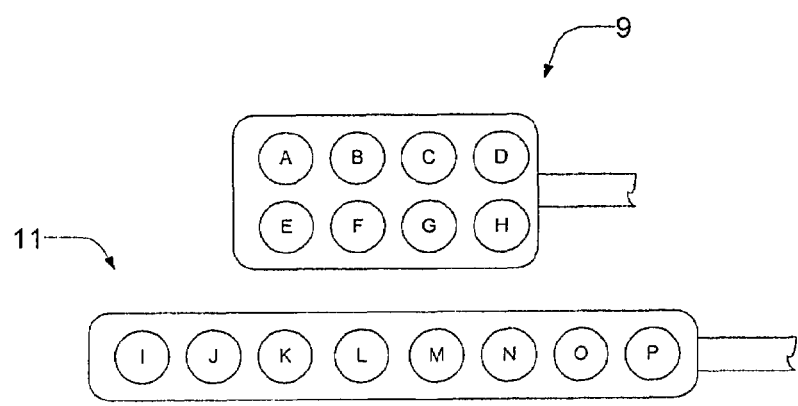
FIG. 2 illustrate two examples of electrode arrays that may be used with a system of the present invention.

Data acquisition and stimulation may be performed using different sets of electrode arrays, the same sets of electrode arrays, or a mixed set of electrodes within the arrays. For example, FIG. 2 shows two exemplary electrode arrays that may be used with the system 2. Electrodes A-H are positioned on a 2×4 grid array 9 and electrodes I-P are positioned on a 1×8 strip electrode array 11. Such electrode arrays may be placed subdurally or epidurally. In some embodiments, the electrode arrays will be positioned over a seizure focus to receive electrical signals from the seizure focus. In many embodiments, it may also be desirable to also deliver electrical stimulation to the same seizure focus. As such, it may be desirable to use the same electrode arrays to both sense and deliver stimulation.

In other configurations it may be desirable to use one electrode array 9 (e.g., electrodes A-H) to sense signals and to use electrode array 11 (e.g., electrodes I-P) to deliver stimulation to the subject. In yet other configurations it may be desirable to use some or all of the electrodes on arrays 9, 11 to sense and to use some or all of the electrodes to deliver stimulation. For example, it may be desirable to use a mixed set of electrodes to sense and stimulate. For example, electrodes A-H of array 9 may be used to sense signals and electrodes B-C-F-G may be used to deliver electrical stimulation. Similarly, electrodes I-M of array 11 may be used to sense signals and electrodes L-P may be used to deliver electrical stimulation.

The systems of the present invention typically include one or more implantable devices or components and one or more external devices or components. However, in other embodiments, the entire system may be implantable within the subject. Any number of the system components can be adapted to be implantable or external to the subject.

The signals sensed by sensing assembly 6 are typically reflective of the subject's brain activity state and/or neural state. Analysis of the brain activity state by the observer algorithm may indicate that the subject is in an inter-ictal state (e.g., a normal state) in which the subject has a low susceptibility to a seizure, a pro-ictal state (e.g., a state that has an increased susceptibility to a seizure), a pre-ictal state (e.g., a state that indicates that a seizure is imminent), an ictal state (e.g., a state in which a seizure is already occurring) or a post-ictal state (e.g., a seizure has ended). As will be described in more detail below, it may be desirable to use such determinations of brain state to modify one or more parameters of the duty cycling, stimulation parameters and/or sensing parameters.

System 2 may be used with closed-loop control systems that are adapted to control the subject's neural state so as to substantially prevent the subject from entering a neural state in which the subject has an elevated susceptibility to a seizure. Delivery of electrical stimulation may be used to maintain the subject's neural state in a state that is at low susceptibility or in cases in which the subject has entered a neural state that has an elevated susceptibility to a seizure, to drive the subject's neural state from the elevated susceptibility to a seizure back down to a neural state that is at a low susceptibility to a seizure.

In order to provide stimulation and sensing of the subject's state, preferred embodiments of the system 2 comprise a timing controller 4 which may be programmed to control the time at which the sensing assembly 6 acquires the signal to be substantially different than the time when the stimulation assembly 8 stimulates the subject. In preferred embodiments the timing controller 4 is in communication with both the sensing assembly and the stimulating assembly, as shown in FIG. 1.

In some embodiments the timing controller 4 is programmed to control the time at which the sensing assembly 6 acquires the signal to be multiple discrete acquisition times and/or to control the time at which the stimulation assembly 8 stimulates the nervous system component to be multiple discrete stimulation times. The multiple discrete acquisition and stimulation times can be of any number and may be of any duration.

Figure 3:
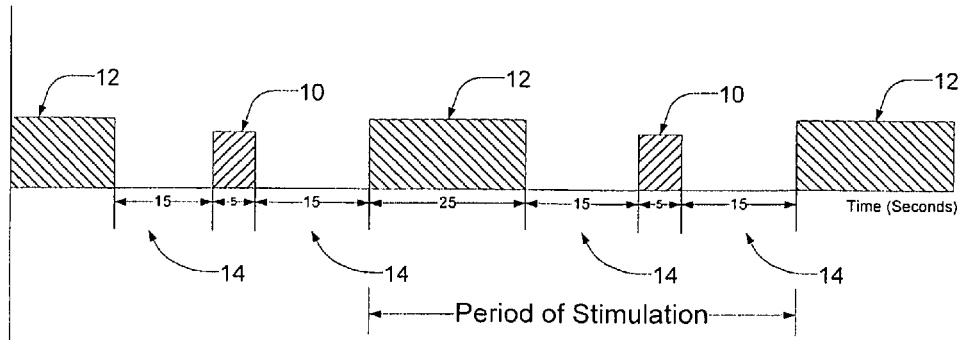
FIG. 3 shows a timeline showing acquisition and stimulation epochs and an exemplary Period of stimulation of the present system.

FIG. 3 illustrates an exemplary amplitude v. time graph showing multiple discrete acquisition epochs 10 and multiple discrete stimulation epochs 12. As shown in FIG. 3, the timing controller can be programmed to control the sensing assembly to acquire the signal in epochs between the stimulation epochs. Also shown in FIG. 3 are epochs of time 14 in between the acquisition epochs and stimulation epochs in which no acquisition or stimulation occurs. As can be seen from FIG. 3, the epochs at which stimulation occurs does not overlap with the epochs at which the acquisition occurs and thus stimulation-induced artifact, or stimulation signal that is sensed by the sensing assembly, is reduced. The system's power consumption can also be minimized by controlling the times at which the system acquires a signal from, and stimulates, the subject.

In some embodiments the timing controller can be programmed to control either the multiple discrete acquisition epochs and/or the multiple discrete stimulation epochs to occur in a regular pattern or adaptively. For example, the multiple discrete acquisition and or stimulation times can occur on a regular cycle or Period, as shown in FIG. 3. While FIG. 3 illustrates an "amplitude" of the stimulation epochs and sensing epochs as being constant, the parameters of the stimulation and sensing epochs may vary from period-to-period, epoch-to-epoch, or the like. The selection of parameters for each of the epochs may be based on a predetermined schedule, based on an analysis of the previously sensed signals from one or more previous epochs, or the like. For example, if the sensed signals are indicative of a neural state that is at an elevated susceptibility of a seizure, the parameters of the sensing within the sensing epoch may be changed (e.g., frequency of sampling EEG signals, duration of the sensing epochs, duration of the epochs between the sensing and stimulation, number of electrode channels being sampled, pre-amplification gain and bandwidth changes, or the like) and/or parameters of stimulation delivered during the stimulation epoch (e.g., duration of stimulation epoch, amplitude, current, voltage, pulse amplitude, pulse width, pulse frequency, pulses per burst, burst frequency, or the like) may be changed.

Some subjects are more prone to having seizures at specific times of day. Consequently, the timing controller may be programmed to automatically adjust the acquisition epochs and stimulation epochs based on time of day. For example, if the subject was known to have a particular vulnerability upon awakening from sleep, the timing controller could be configured to increase a duty cycle of sensing epochs in the morning hours.

In addition to the modification of the parameters within the epochs, the Period of the stimulation signal (as shown in FIG. 3) can also be increased or decreased. The increase or decrease of the Period of the stimulation signal may be based on processing of any of the previous acquisition epochs. For example, if the sensed signals are indicative of a neural state that is at an elevated susceptibility of a seizure, the Period of stimulation may be decreased in an attempt to quickly return the neural state to a more "normal" state (e.g., the stimulation epochs or parameters of the stimulation may be increased and the stimulation epochs of the sensing may be decreased).

Figure 4:
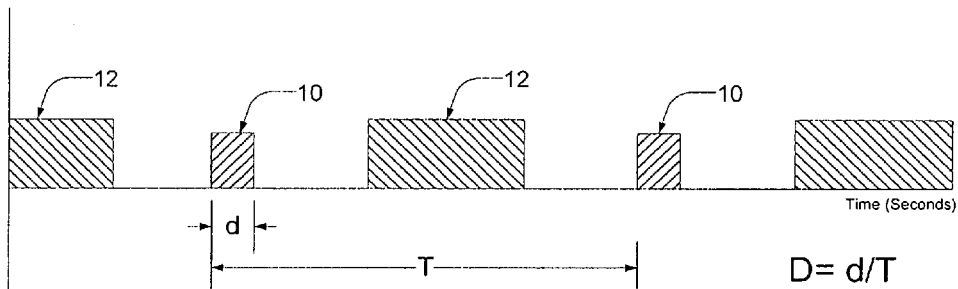
FIG. 4 illustrates an acquisition duty cycle.

The scheduling of acquisition epochs and/or the stimulation epochs may be based on a duty cycle. Duty cycle as used herein refers to the ratio of the duration of the event in a given Period to the Period. As shown in FIG. 4, the duty cycle of the acquisition times is given as the duration of the event "d" divided by the Period "T" of the event, or d/T. The acquisition and/or stimulation duty cycle can be varied as necessary according to the purposes of the invention. The Period of the stimulation signal as shown in FIG. 3 is 60 seconds In FIG. 3, the duty cycle of the stimulation signal is 5/60. The duty cycle can be increased, e.g., by increasing the value of "d," while maintaining a constant value of "T," or by maintaining a constant value of "d" and decreasing the value of "T." Similarly, the duty cycle can be decreased.

The lengths of the data acquisition epochs, stimulation epochs and Period may vary from subject to subject and may vary based on the particular disorder being treated. For example, for treating epilepsy, the acquisition epoch is typically between about 0.25 seconds to about 5 minutes, preferably between about 1 second to about 30 seconds, and more preferably about 5 seconds. The stimulation epochs are typically between about 0.5 seconds to about 5 minutes, preferably between about 1 seconds and about 30 seconds, and most preferably about 20 seconds. As noted above, in some embodiments it may be desirable to have epochs of time between the data acquisition and stimulation epochs in which the system does not acquire signal from or deliver stimulation to the subject. The duration of these epochs of time is typically between 0.25 seconds and about 10 seconds, preferably between about 1 seconds and about 5 seconds, and most preferably about 4 seconds, but the length of such epochs may depend on the recovery of electrodes from voltage offsets caused by stimulation activity and/or by the acquisition and/or stimulation time programmed into the timing controller.

Figure 5:
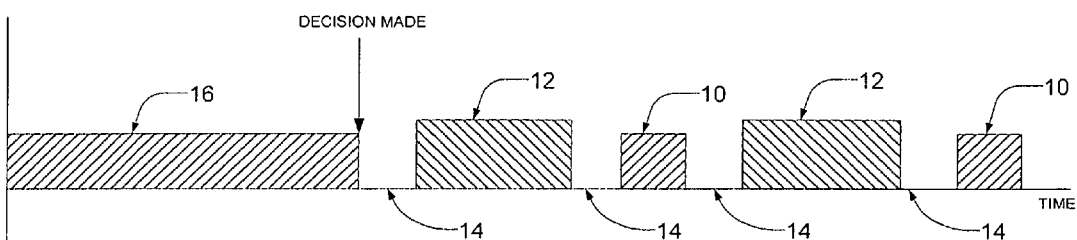
FIG. 5 shows a duty cycling method with a seizure prediction/detection algorithm.

The duty cycling methods described above are equally applicable to systems whose observer algorithms are adapted for seizure prediction and seizure detection. In the seizure prediction/detection systems, neuromodulation (e.g., electrical stimulation) may only be delivered to the subject when it is determined that the subject has an elevated susceptibility for a seizure (e.g., a seizure is predicted). As shown in FIG. 5, such systems will acquire brain activity signals 16 (e.g., EEG) on a substantially continuous basis from the subject and analyze the brain activity signals in substantially real-time to estimate the subject's propensity for a seizure. If the observer algorithm determines that the subject has an elevated susceptibility for a seizure (e.g., seizure prediction—indicated in FIG. 5 as "Decision Made"), the duty cycling of the stimulation epochs 12 and data acquisition epochs 10 (as described above) may be initiated by the timing controller. In such embodiments, the duty cycling may follow a predetermined schedule (described above) or it may be adaptive to the subject's observed brain activity state.

The observer algorithms of the devices may be adapted to continue to analyze the discontinuous epochs of data to estimate the subject's susceptibility to a seizure while stimulation is initiated. By duty cycling the data acquisition and stimulation epochs, the seizure prediction and seizure detection devices are able to analyze the brain activity signals determine if the stimulation is effective in mitigating the subject's susceptibility to a seizure, while still reducing artifact in the sensed signals. While not shown in FIG. 5, if analysis of the discontinuous data acquisition epochs 10 shows that the subject no longer has an elevated susceptibility for a seizure, the device may be configured to revert back to the substantially continuous acquisition of brain activity signals 16 or a different duty cycle.

If however, the observer algorithm determines that the stimulation epochs have not reduced the subject's susceptibility for a seizure, a number of different actions could be carried out. First, the stimulation epochs may be continued using the same stimulation parameters and duty cycled with the data acquisition epochs. Second, one or more parameters of the duty cycling may be varied. For example, it may be useful to increase a duration of the stimulation epochs and/or reduce a duration of the data acquisition epochs and/or the epochs between the stimulation epoch and data acquisition epochs. Third, one or more parameters of the stimulation epoch may be automatically adaptively varied in an attempt to find a combination of parameters that are effective for the particular subject. If a certain combination of stimulation parameters are able to affect the subject's brain activity state better than other combinations of parameters, such parameters may be stored in memory and used for subsequent stimulation epochs.

The observer algorithm may be embodied in a device that is implanted in the subject, embodied in a device that is external to the subject, or in separate modules in both the implanted unit and external device. The observer algorithm may be used to analyze the subject's brain activity so as to determine the appropriate control signal, determine the subject's susceptibility to a seizure, predict/detect a seizure, and facilitate delivery of an appropriate electrical stimulation to the subject.

Figure 6:
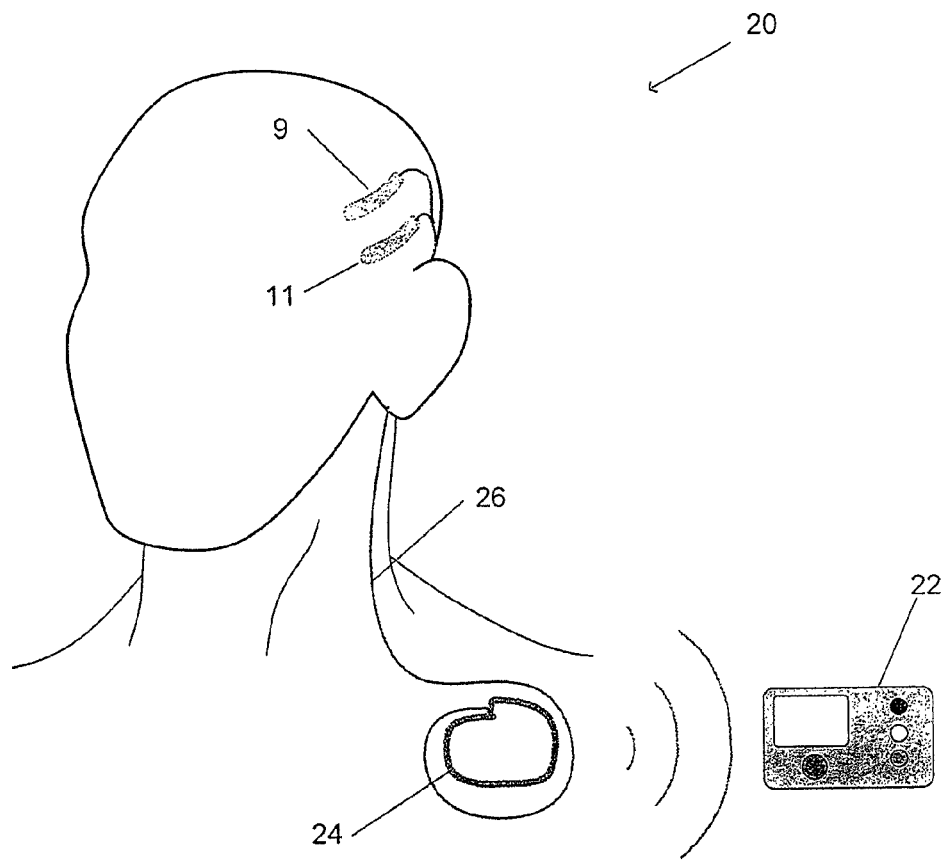
FIG. 6 shows an exemplary system of the present invention.

FIG. 6 illustrates one preferred embodiment in which the observer algorithm is in a device that is external to the subject. However, as described in pending commonly owned U.S. patent application Ser. Nos. 11/321,897 and 11/322,150, both filed Dec. 28, 2005, the observer algorithms of the present invention may be disposed anywhere within the system. In the embodiments in which the observer algorithm is external to the subject, the signals (EEG) are substantially continuously sampled by electrode arrays 9, 11 and sent to the sensing assembly in an implanted unit 24. The samples are subsequently transmitted to the external device 22 via the implanted unit 24.

The electrode arrays 9, 11 will be configured to sample the brain activity of the groups of neurons in the immediate vicinity of the electrode arrays 9, 11. The electrode arrays 9, 11 are electrically joined via cables 26 to the implanted unit 24. In one embodiment, the electrode arrays 9, 11 are implanted intracranially and the cables 26 are tunneled beneath the skin through the neck to the implanted unit 24 that is implanted in a subclavicular cavity of the subject. In alternative embodiments, the cables 26 and unit 24 may be attached to the subject externally.

In one embodiment, the implanted unit 24 is configured to facilitate the sampling of signals from the electrodes 9, 11. Sampling of brain activity is typically carried out at a rate above about 200 Hz, and preferably between about 200 Hz and about 1000 Hz, and most preferably at about 400 Hz. The sampling rates could be higher or lower, depending on the specific conditions being monitored, the subject, and other factors. Each sample of the subject's brain activity is typically encoded using between about 8 bits per sample and about 24 bits per sample, and preferably about 16 bits per sample.

In alternative embodiments, the implanted unit 24 may be configured to monitor the signals on a non-continuous basis. In such embodiments, signals may be monitored periodically or aperiodically.

The external data analysis/collection device 22 is preferably carried external to the body of the subject. The external device 22 can be a computer system, such as, e.g., a personal computer, handheld device, physician programmer, or the like. The external device 22 receives and stores signals, including EEG signals and possibly other physiological signals, from the implanted unit 24. Communication between the external data device 22 and the implanted unit 24 may be carried out through wireless communication, such as an infrared link, ultrasonic link, inductive link, radiofrequency link, or the like. The wireless communication link between the external data device 22 and the implanted unit 24 is typically a two-way communication link for transmitting data but could be a one-way communication link. For example, the external device and implanted unit could include both a two-way inductive link (short distance magnetic loop coupling) and a one-way RF link for sending alerts to the subject.

In alternative embodiments, it may be desirable to have a direct communications link from the external data device 22 to the implanted unit 24, such as, for example, via an interface device positioned below the subject's skin. The interface (not shown) may take the form of an adhesively or magnetically attached transducer that would enable power to be continuously delivered to the implanted unit 24 and would provide for relatively higher rates of data transmission. Error detection and correction methods may be used to help insure the integrity of transmitted data. If desired, the wireless data signals can be encrypted prior to transmission to the external data device 22.

Figure 7:
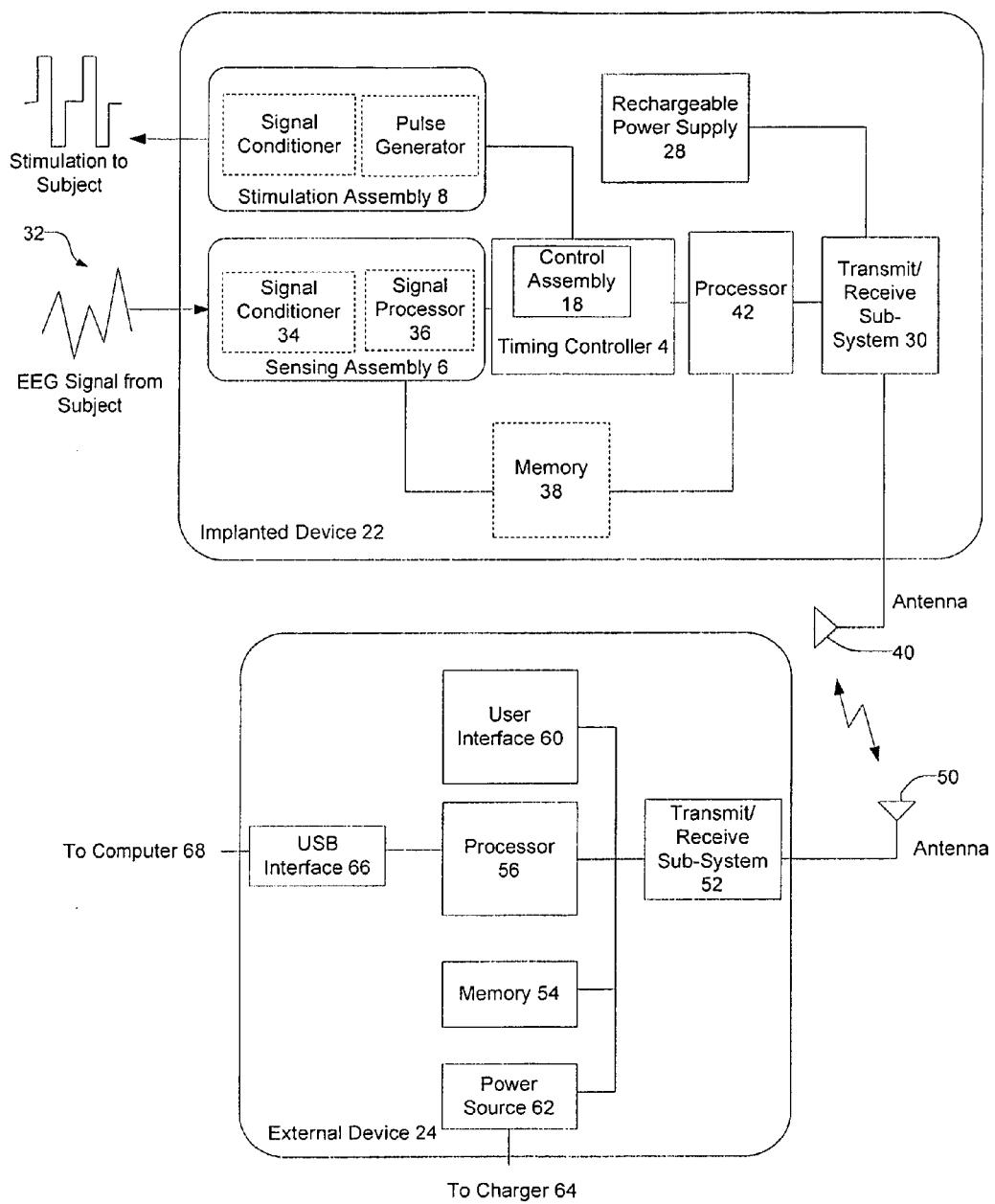
FIG. 7 shows components of an implanted unit and components of an external device.

The implanted unit 24 may optionally comprise electronic component systems as depicted schematically in FIG. 7. Energy for the system is supplied by a rechargeable power supply 28 (or a non-rechargeable power supply). The rechargeable power supply may be a battery, or the like. The rechargeable power supply 28 may also be in communication with a transmit/receive sub-system 30 so as to receive power from outside the body by inductive coupling, radiofrequency (RF) coupling, etc. Power supply 28 will generally be used to provide power to the other components of the implantable device. Signals 32 from the electrode array 9, 11 are received by sensing assembly 6 of the implanted unit 24. The signals may be initially conditioned by a signal conditioner 34 (e.g., an amplifier, a filter, and an analog-to-digital converter, etc.) and/or other signal processors 36 of the sensing assembly 6.

The amplifiers may be one or more single amplifiers or a multi-channel amplifiers depending upon the number of electrodes with which it interfaces. In some embodiments, the amplifiers are physically located in the same enclosure as the filters that is, in a single signal conditioner. The amplifiers may also be located separately from the filters. For example, the amplifier may be affixed to or situated adjacent to an associated electrode array. This arrangement facilitates the pre-amplification of the associated signals generated by the associated electrode arrays, which increases the signal-to-noise ratio of the acquired signals. The amplifiers may be any known voltage amplifier now or later developed suitable for amplifying the particular signals generated by an associated electrode or electrode array.

The amplified signal may then be passed to an associated filter. The filter can be physically separate from or incorporated into sensing assembly. The filter may be a low pass filter. The low pass filter typically has a cut-off frequency of 1000 Hz, preferably of 300 Hz, and most preferably of 150 Hz. In addition to or as an alternative to the low-pass filter, the device may include a notch filter to remove, for example, 50 or 60 Hz noise, or other types of filters appropriate for the type of signals acquired by an associated electrode arrays.

In preferred embodiments the sensing assembly also includes a signal processor or other dedicated hardware for further processing the conditioned signal. The signal processor can be implemented in, e.g., a fast microprocessor, a DSP (digital signal processor) chip, ASIC, or as analog circuitry. The signal processor (and any of the other signal processors described herein) may include multiple cores so as to improve processing throughput, while further reducing power consumption. The signal processor can include a separate signal processor for each conditioned signal which can be input if a plurality of electrodes acquire signal from the subject. Such signal processors may be used to filter, extract features from, transform, generate statistics for, or encrypt the sampled signals.

A memory module 38 may be provided for storage of some or all of the sampled signals prior to transmission via a transmit/receive sub-system 30 and antenna 40 to the external data device 22. For example, the memory module 40 may be used as a buffer to temporarily store the conditioned signals from the electrode arrays 9, 11 if there are problems with transmitting data to the external data device 22, such as may occur if the external data device 22 experiences power problems or is out of range of the communications system. The external data device 22 can be configured to communicate a warning signal to the subject in the case of data transmission problems to inform the subject and allow him or her to correct the problem. Memory module 38 may also be used to permanently store a portion or all of the sampled EEG signals, if desired.

The implanted unit 24 may optionally comprise dedicated circuitry of a digital or analog or combined digital/analog nature, ASIC, DSP and/or a fast microprocessor, referred to herein collectively as "processor" 42, for further processing the signals prior to transmission to the external data device 22. In some embodiments, the processor 42 may execute one or more observer algorithms such as, neurological event prediction or detection algorithms, seizure prediction algorithms, seizure detection algorithms, or portions of such algorithms. For example, in some configurations, the processor 42 may run one or more feature extractors that extract features from the EEG signal that are relevant to the purpose of monitoring. Thus, if the system is being used for diagnosing or monitoring epileptic subjects, the extracted features (either alone or in combination with other features) may be indicative or predictive of a seizure. Once the feature(s) are extracted, the processor 42 may transmit the extracted feature(s) to the external data device 22 and/or store the extracted feature(s) in memory 38. Because the transmission of the extracted features is likely to include less data than the EEG signal itself, such a configuration will likely reduce the bandwidth requirements for the communication link between the implanted unit 24 and the external data device 22.

FIG. 7 also illustrates some of the components that may be included in the external device 22. Signals from the implanted unit 24 are received at an antenna 50 and conveyed to a transmit/receive sub-system 52. The signals received may include a raw EEG signal, a processed EEG signal, extracted features from the EEG signal, a result from EEG analysis software that ran on the implanted processor 42, or any combination thereof.

The received data may thereafter be stored in memory 54, such as a hard drive, RAM, EEPROM, flash memory, or the like and/or processed by a microprocessor, ASIC, DSP, or other dedicated circuitry of a digital or analog or combined digital/analog nature, referred to herein collectively as a "processor" 56. Processor 56 may be configured to request that the implanted unit 24 perform various checks or calibrations prior to signal recording and/or at specified times to ensure the proper functioning of the system.

Data may be transmitted from memory 54 to processor 56 where the data may optionally undergo additional processing. For example, if the EEG data is encrypted, it may be decrypted. The processor 56 may also comprise one or more filters that filter out high-frequency artifacts (e.g., muscle movement artifacts, eye-blink artifacts, chewing, etc.) so as to prevent contamination of the high frequency components of the sampled EEG signals. In some embodiments, the processor 56 may process the EEG data to detect seizures, predict the onset of a future seizure, generate metrics/measurements of seizure activity, or the like as described below.

External data device 22 will typically include a user interface 60 for displaying outputs to the subject and for receiving inputs from the subject. The user interface will typically comprise outputs such as auditory devices (e.g., speakers) visual devices (e.g., LCD display), tactile devices (e.g., vibratory mechanisms), or the like, and inputs, such as a plurality of buttons, a touch screen, and/or a scroll wheel.

The user interface may be adapted to allow the subject to indicate and record certain events. For example, the subject may indicate that medication has been taken, the dosage, the type of medication, meal intake, sleep, drowsiness, occurrence of an aura, occurrence of a seizure, or the like. Such inputs may be used in conjunction with the recorded data to improve the off-line or on-line analysis of the subject's condition and determine the efficacy of the medications taken by the subject.

The LCD display may be used to output a variety of different communications to the subject including, status of the device (e.g., memory capacity remaining), battery state of one or more components of system, whether or not the external data device 22 is within communication range of the implanted unit 24, a warning (e.g., a seizure warning), a prediction (e.g., a seizure prediction), a recommendation (e.g., "take medicine"), or the like. Of course, it may be desirable to provide an audio output or vibratory output to the subject in addition to or as an alternative to the visual display on the LCD.

External data device 22 may also include a power source 62 or other conventional power supply that is in communication with at least one other component of external data device 22. The power source 62 may be rechargeable. If the power source 62 is rechargeable, the power source may optionally have an interface for communication with a charger 64. External data device 22 may also include a communication interface 66 for coupling to a remote computer 68 (e.g., a physician's computer workstation). While not shown in FIG. 7, external data device 22 will typically comprise a clock circuit (e.g., oscillator and frequency synthesizer) to provide the time base for synchronizing the external data device 22 and the implanted unit 24.

In a preferred embodiment, most or all of the processing of the signals received by the implanted unit 24 is done in an external data device 22 that is external to the subject's body. In such embodiments, the implanted unit 24 would receive the signals from subject and may or may not pre-process the signals and transmit some or all of the measured signals transcutaneously to an external data device 22, where the observer algorithm processes the EEG data. Advantageously, such embodiments reduce the amount of computational processing power that needs to be implanted in the subject, thus potentially reducing power consumption and increasing battery life. Furthermore, by having the processing external to the subject, the judgment or decision making components of the system may be more easily reprogrammed or custom tailored to the subject without having to reprogram the implanted unit 24.

In alternative embodiments, the observer algorithms disclosed herein and treatment algorithms responsive to the predictive algorithms may be embodied in a device that is implanted in the subject's body or the algorithm may be modular and some modules may be implanted in the subject's body and other modules may be external to the subject's body. For example, in one embodiment the observer algorithm may be stored in and processed by the implanted unit 24. A treatment algorithm, in contrast, may be processed in a processor that is embodied in an external data device 22 external to the subject's body. In such embodiments, the subject's propensity for seizure characterization (or whatever output is generated by the observer algorithm) is transmitted to the external device 22, and the processor performs any remaining processing to generate and display the output from the observer algorithm and communicate this to the subject. Such embodiments have the benefit of sharing processing power, while reducing the communications demands on the implanted unit 24. Furthermore, because the treatment algorithm is external to the subject, updating or reprogramming the treatment algorithm may be carried out more easily.

In other embodiments, the signals 32 may be processed in a variety of ways in the implanted unit 24 before transmitting data to the external data device 22 so as to reduce the total amount of data to be transmitted, thereby reducing the power demands of the transmit/receive sub-system 30. Examples include: digitally compressing the signals before transmitting them; selecting only a subset of the detected signals for transmission; selecting a limited segment of time and transmitting signals only from that time segment; extracting salient features of the signals and transmitting data representative of those features rather than the signals themselves. Further processing and analysis of the transmitted data may take place in the external data device 22.

It may be possible to perform some of the processing in the implanted unit 24 and some of the processing in the external data device 22. For example, one or more features from the one or more signals may be extracted with feature extractors in the implanted unit 24. Some or all of the extracted features may be transmitted to the external data device 22 where the features may be classified to predict the onset of a seizure, or the like. If desired, external data device 22 may be customizable to the individual subject. Consequently, the classifier may be adapted to allow for transmission or receipt of only the features from the implanted unit 24 that are predictive for that individual subject. Advantageously, by performing feature extraction in the implanted unit 24 and classification in an external device at least two benefits may be realized. First, the amount of wireless data transmitted from the implanted unit 24 to the external data device 22 is reduced (versus transmitting pre-processed data). Second, classification, which embodies the decision or judgment component, may be easily reprogrammed or custom tailored to the subject without having to reprogram the implanted unit 24.

In yet another embodiment, it may be possible to switch the positions of the classifier and the feature extractors so that feature extraction may be performed external to the body. Pre-processed signals (e.g., filtered, amplified, converted to digital) may be transcutaneously transmitted from implanted unit 24 to the external data device 22 where one or more features are extracted from the one or more signals with feature extractors. Some or all of the extracted features may be transcutaneously transmitted back into the implanted unit 24, where a second stage of processing may be performed on the features, such as classifying of the features (and other signals) to characterize the subject's propensity for the onset of a future seizure. If desired, to improve bandwidth, the classifier may be adapted to allow for transmission or receipt of only the features from the subject communication assembly that are predictive for that individual subject. Advantageously, because feature extractors may be computationally expensive and power hungry, it may be desirable to have the feature extractors external to the body, where it is easier to provide more processing and larger power sources.

The output from the observer algorithm (i.e., brain activity state measurement, "yes" seizure, "no" seizure, normal susceptibility, elevated susceptibility, etc.) may be used by a control assembly 18 of the timing controller 4 to initiate duty cycling, adjust parameters of the duty cycling, and/or determine the parameters of a subsequent neuromodulation signal transmitted to the subject (if any). For example, the control assembly 18 may be adapted to adjust the acquisition epochs and/or stimulation epochs from the acquisition epochs and/or stimulation epochs programmed into the timing controller 4 for the duty cycle.

As noted above, the control assembly 18 can also be adapted to dynamically adjust the stimulation and/or acquisition epochs of the duty cycle. Dynamic adjustments to the timing controller can be accomplished using the closed-loop feedback system described herein. The sensing assembly can acquire a signal from the subject indicative of the subject's brain activity response to a previously delivered stimulation signal. Based on the acquired signal, or parameters thereof, the control assembly can dynamically adjust any of the timing parameters stored in the timing controller, e.g., the duty cycle of the acquisition and/or stimulation epoch.

In alternative embodiments of the present invention, one of the signal processors 42, 56 of the system may include at least one observer algorithm which is configured to be controlled by the timing controller to run and process data acquired by, e.g., an electrode array, at a specified time or times.

In some configurations, the observer algorithm is configured to be controlled by the timing controller 4 to process signal data only at specified times. The times at which such processing occurs can be synchronized with the time at which a sensing electrode array is acquiring a signal from the subject, such that a signal is acquired by the subject and the corresponding signal is received and processed by the observer algorithm to generate an output. The observer algorithm will thus be controlled by the timing controller not to run and process data at specified times. The sensing electrode array can again be synchronized not to acquire any signal from the subject during the time at which the observer algorithm is not running and processing data. Thus, in some embodiments, the sensing electrode array and the observer algorithm can be controlled to be operating at substantially the same time. Controlling when these components are operating and thus receiving power from the system helps control the system's power consumption and can increase the life of the system.

It is further contemplated that one or more of the components of the sensing assembly can also be configured to be controlled by the timing controller 4 to run/operate at specified times. In such embodiments the one or more components can be controlled to run at the same, substantially the same or different times depending on the component. For example, it may be advantageous for the sensing electrode array to acquire a signal from the subject, but rather than analyze the sampled signals immediately, to store the acquired signal in memory module 38, 54 until a later time when the observer algorithm can process the data. For example, a sensing electrode array could be controlled to acquire a signal from a subject based on a specified duty cycle, while the observer algorithm is controlled to process data based on a different duty cycle the sensing electrode.

The control assembly 18 receives an output from the observer algorithm, e.g., a neural state of the subject, seizure prediction, susceptibility to seizure, etc. The control assembly 18 is configured to then determine and/or adjust parameter(s) of the stimulation signal to be delivered to the subject. The stimulation signal to be generated, as determined by the control assembly, is output to the stimulation assembly 8, including the signal generator which generates the stimulation signal. In one embodiment, the control assembly is a state machine, utilizing current and past system behavior in the determination and calculation of a stimulation signal.

The control assembly may calculate waveform parameters of the stimulation signal to be delivered, including, e.g., pulse amplitude, pulse width, pulse frequency, pulses per burst, and burst frequency. Alternatively, the waveform parameters may already be predetermined based on prior physician input. The control assembly can also select between the regulation of pulse voltage or pulse current as the regulated pulse amplitude.

The stimulation assembly 8, shown in FIGS. 1 and 7, receives the output from the control assembly 18. The stimulation assembly 8 can comprise a pulse generator 44 and signal conditioner 46 (e.g., an output amplifier, therapy power supply, output multiplexer, DC balancing or blocking circuit or the like). The pulse generator generates, based on the output received from the control assembly, one or more stimulus waveforms, each of which is characterized by several parameters, e.g., pulse amplitude, pulse width, pulse frequency, number of pulses per burst, and burst frequency. As noted above, pulse amplitude may comprise pulse voltage or pulse current. Preferably, each of these parameters can be independently varied, as specified by the output from the control assembly. As noted, the stimulus waveforms comprising the stimulation signal generated by the stimulation assembly are applied to the subject via the electrode array. The pulse generator generates a single waveform when single channel stimulation is to be used, and a plurality of waveforms when multiple channel stimulation is to be used. The pulse generator may generate monophasic, biphasic waveforms, or multiphasic waveforms, with or without DC current and deliver such waveforms to the stimulation electrode array. The stimulation waveforms may be delivered directly to the brain tissue (e.g., epidural, subdural, deep brain tissue, etc.), to cranial nerves, peripheral nerves, and/or to other nervous system or non-nervous system components.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention For example, while preferred embodiments incorporate a timing controller, alternate embodiments of the present invention may not include a central timing controller, and the stimulation may be designed to always have sufficient inactive epochs between stimulation epochs, and the sensing assembly of the system of the present invention can determine on its own when stimulation artifact is causing a problem and disqualify that portion of the signal, (e.g., the sensing assembly will have the capability to determine when stimulation is not occurring).

It is intended that the following claims define the scope of the invention and that methods and structures within the scope of these claims and their equivalents be covered thereby.

What is claimed is:

1. A system to reduce artifact in a signal acquired from a subject, the system comprising:
   a sensing assembly adapted to acquire a signal from a subject indicative of the subject's brain activity;
   a stimulation assembly adapted to stimulate one or more neurons of the subject; and
   a timing controller programmed to control the time the sensing assembly is powered to acquire the signal such that the sensing assembly is powered at a substantially different time than the time when the stimulation assembly stimulates the subject and that the sensing assembly is not powered to acquire the signal during the time the stimulation assembly stimulates the subject,
   wherein the acquisition time and the stimulation time are variable based upon the subject's predicted susceptibility to having a seizure.

2. The system of claim 1 wherein the timing controller is programmed to control the time at which the sensing assembly acquires the signal to be multiple discrete acquisition times and to control the time at which the stimulation assembly stimulates the one or more neurons to be multiple discrete stimulation times.

3. The system of claim 2 wherein the timing controller is programmed to control the sensing assembly to acquire the signal in between the stimulation assembly stimulating the one or more neurons.

4. The system of claim 2 wherein each of the multiple discrete acquisition times are about 0.25 seconds to about 5 minutes.

5. The system of claim 4 wherein each of the multiple discrete acquisition times are about 1 second to about 30 seconds.

6. The system of claim 2 wherein each of the multiple discrete stimulation times are about 0.5 seconds to about 5 minutes.

7. The system of claim 6 wherein each of the multiple discrete stimulation times are about 1 second to about 30 seconds.

8. The system of claim 2 wherein the system further comprises a control assembly adapted to adjust the multiple discrete acquisition times and the multiple discrete stimulation times.

9. The system of claim 8 wherein the control assembly is in communication with a device external to the subject, wherein the device is adapted to allow adjustment of the stimulation and acquisition times.

10. The system of claim 8 wherein the control assembly is adapted to dynamically adjust the stimulation or acquisition times.

11. The system of claim 1 wherein the acquisition time and the stimulation time provide an epoch of time between the acquisition time and stimulation time in which no acquisition or stimulation occurs.

12. The system of claim 11 wherein each epoch of time between the acquisition times and stimulation times in which no acquisition or stimulation occurs is about 0.25 seconds to about 10 seconds.

13. The system of claim 12 wherein each epoch of time between the acquisition times and stimulation times in which no acquisition or stimulation occurs is about 1 second to about 5 seconds.

14. The system of claim 1 wherein the sensing assembly and the stimulation assembly each comprise an electrode array.

15. The system of claim 14 wherein the same electrode array is used to stimulate the one or more neurons and acquire the signal from the subject.

16. The system of claim 14 wherein the stimulation assembly comprises an electrode array adapted to be coupled to a peripheral nerve.

17. The system of claim 16 wherein the peripheral nerve is a vagus nerve.

18. The system of claim 1 wherein the signal is an EEG signal from the subject.

19. The system of claim 1 wherein the subject's brain activity is analyzed to predict an onset of a seizure.

20. The system of claim 1 further comprising a signal processor in communication with the sensing assembly adapted to process the signal to estimate an epileptic neural state.

21. The system of claim 20 wherein the signal processor comprises an observer algorithm operative when the sensing assembly is acquiring the signal.

22. The system of claim 21 wherein the observer algorithm comprises one or more feature extractors and a classifier.

23. The system of claim 1 wherein the timing controller is programmed to increase a parameter of the stimulation when the subject has a predicted elevated susceptibility for having a seizure.

24. The system of claim 23 wherein the timing controller is programmed to increase the stimulation frequency when the subject has a predicted elevated susceptibility for having a seizure.

25. The system of claim 1 wherein the timing controller is programmed to initiate stimulation when the subject has a predicted elevated susceptibility for having a seizure.

26. The system of claim 1 wherein the timing controller is programmed to decrease a parameter of the stimulation when the subject has a predicted reduced susceptibility for having a seizure.

27. A method of reducing artifact in a signal acquired from a subject, the method comprising:
powering signal acquisition circuitry to acquire a signal from a subject indicative of the subject's brain activity;
stimulating the subject;
controlling the time during which the powering signal acquisition circuitry occurs such that the signal acquisition circuitry is powered at a substantially different time than the time during which stimulating the subject occurs and that the signal acquisition circuitry is not powered to acquire the signal during said stimulating the subject; and
varying the acquiring time and the stimulating time based upon the subject's predicted susceptibility to having a seizure.

28. The method of claim 27 wherein the powering comprises acquiring the signal at multiple discrete acquisition times and the stimulating comprises stimulating the one or more neurons at multiple discrete stimulation times.

29. The method of claim 28 wherein the powering occurs between the stimulating the subject.

30. The method of claim 29 further comprising adjusting the multiple discrete acquisition times and/or the multiple discrete stimulation times.

31. The method of claim 28 wherein each of the multiple discrete acquisition times are about 0.25 seconds to about 5 minutes.

32. The method of claim 31 wherein each of the multiple discrete acquisition times are about 1 to about 30 seconds.

33. The method of claim 28 wherein each of the multiple discrete stimulation times are about 0.5 seconds to about 5 minutes.

34. The method of claim 33 wherein the multiple discrete stimulation times are about 1 to about 30 seconds.

35. The method of claim 28 wherein the acquiring comprises acquiring an EEG signal from the subject.

36. The method of claim 28 wherein the stimulating comprises stimulating a peripheral nerve.

37. The method of claim 36 wherein the peripheral nerve is a vagus nerve.

38. The method of claim 28 wherein the subject's brain activity is processed to measure the subject's susceptibility to a seizure.

39. The method of claim 28 further comprising processing the signal to estimate an epileptic neural state.

40. The method of claim 28 wherein each epoch of time between acquisition times and stimulation times in which no acquisition or stimulation occurs is about 0.25 seconds to about 10 seconds.

41. The method of claim 40 wherein each epoch of time between acquisition times and stimulation times in which no acquisition or stimulation occurs is about 1 second to about 5 seconds.

42. The method of claim 27 wherein the varying step comprises increasing a stimulating parameter based upon a predicted elevated susceptibility to having a seizure.

43. The method of claim 42 wherein increasing a stimulating parameter based upon an elevated predicted susceptibility to having a seizure comprises increasing the stimulation frequency based upon a predicted elevated susceptibility to having a seizure.

44. The method of claim 27 wherein the varying step comprises initiating stimulation based upon a predicted elevated susceptibility to having a seizure.

45. The method of claim 27 wherein the varying step comprises decreasing a stimulation parameter based upon a predicted reduced susceptibility to having a seizure.

46. A method of managing seizures, the method comprising:
acquiring an EEG signal from a subject during multiple discrete acquisition times;
stimulating one or more neurons of the subject during multiple discrete stimulation times;
controlling the time during which signal acquisition circuitry is powered to acquire the EEG signal such that the signal acquisition circuitry is powered at a substantially different time than the time during which the stimulating occurs and that the signal acquisition circuitry is not powered to acquire the EEG signal during the time the stimulating occurs; and varying the acquisition times and the stimulation times based upon the subject's predicted susceptibility to having a seizure.

47. The method of claim 46 wherein the varying step comprises increasing a stimulating parameter based upon a predicted elevated susceptibility to having a seizure.

48. The method of claim 46 wherein the varying step comprises decreasing a stimulating parameter based upon a predicted reduced susceptibility to having a seizure.

49. The method of claim 46 wherein each of the multiple discrete acquisition times are about 0.25 seconds to about 5 minutes.

50. The method of claim 49 wherein each of the multiple discrete acquisition times are about 1 to about 30 seconds.

51. The method of claim 46 wherein each of the multiple discrete stimulation times are about 0.5 seconds to about 5 minutes.

52. The method of claim 51 wherein each of the multiple discrete stimulation times are about 1 to about 30 seconds.

53. The method of claim 46 wherein epochs of time between acquisition times and stimulation times in which no acquisition or stimulation occurs are about 0.25 seconds to about 10 seconds each.

54. The method of claim 53 wherein epochs of time between acquisition times and stimulation times in which no acquisition or stimulation occurs are about 1 second to about 5 seconds each.

* * * * *

UNITED STATES PATENT AND TRADEMARK OFFICE
CERTIFICATE OF CORRECTION

| | | |
|---|---|---|
| PATENT NO. | : 8,295,934 B2 | Page 1 of 1 |
| APPLICATION NO. | : 11/599179 | |
| DATED | : October 23, 2012 | |
| INVENTOR(S) | : Kent Leyde | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 239 days.

Signed and Sealed this
Thirtieth Day of September, 2014

Michelle K. Lee
*Deputy Director of the United States Patent and Trademark Office*